US012781204B2

(12) United States Patent
Zheng et al.

(10) Patent No.: US 12,781,204 B2
(45) Date of Patent: Nov. 3, 2026

(54) POLYPEPTIDE WITH ASPARTATE KINASE ACTIVITY AND USE THEREOF IN PRODUCTION OF AMINO ACID

(71) Applicant: Tianjin Institute of Industrial Biotechnology, Chinese Academy of Sciences, Tianjin (CN)

(72) Inventors: Ping Zheng, Tianjin (CN); Jiao Liu, Tianjin (CN); Yu Wang, Tianjin (CN); Wenjuan Zhou, Tianjin (CN); Jibin Sun, Tianjin (CN); Jiuzhou Chen, Tianjin (CN); Yanhe Ma, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 613 days.

(21) Appl. No.: 18/030,228

(22) PCT Filed: Sep. 9, 2021

(86) PCT No.: PCT/CN2021/117492
§ 371 (c)(1),
(2) Date: Apr. 4, 2023

(87) PCT Pub. No.: WO2022/078127
PCT Pub. Date: Apr. 21, 2022

(65) Prior Publication Data

US 2023/0332116 A1 Oct. 19, 2023

(30) Foreign Application Priority Data

Oct. 16, 2020 (CN) .......................... 202011110184.9

(51) Int. Cl.
*C12N 9/12* (2006.01)
*C12P 13/08* (2006.01)

(52) U.S. Cl.
CPC ............ *C12N 9/1217* (2013.01); *C12P 13/08* (2013.01); *C12Y 207/02004* (2013.01)

(58) Field of Classification Search
None
See application file for complete search history.

(56) References Cited

U.S. PATENT DOCUMENTS

| | | | |
|---|---|---|---|
| 7,160,711 B2 | 1/2007 | Bathe et al. | |
| 7,345,220 B2 | 3/2008 | Falco | |
| 9,896,734 B2 | 2/2018 | Yue et al. | |
| 9,938,546 B2 | 4/2018 | Lee et al. | |
| 2011/0071274 A1* | 3/2011 | Goerlich ................ | B01J 20/289 530/344 |
| 2015/0337346 A1 | 11/2015 | Yue et al. | |
| 2019/0194630 A1 | 6/2019 | Bradshaw et al. | |

FOREIGN PATENT DOCUMENTS

| | | |
|---|---|---|
| CN | 1748031 | 3/2006 |
| CN | 103773745 | 5/2014 |
| CN | 104099308 | 10/2014 |
| CN | 104334728 | 2/2015 |
| CN | 106062176 | 10/2016 |
| CN | 108486082 | 9/2018 |
| CN | 109295028 | 2/2019 |
| CN | 112111469 | 12/2020 |
| EP | 1394257 | 3/2004 |
| EP | 1590463 | 11/2005 |
| WO | WO 2003014330 A2 | 2/2003 |
| WO | WO 2004/069996 | 8/2004 |
| WO | WO 2015103497 A1 | 7/2015 |
| WO | WO 2020139974 A1 | 7/2020 |

OTHER PUBLICATIONS

Chichili et al. Protein Sci. Dec. 6, 2012;22(2):153-167. doi: 10.1002/pro.2206 (Year: 2012).*

Bornscheuer et al. Curr Protoc Protein Sci. Nov. 2011;Chapter 26:Unit26.7. (Year: 2011).*

Accession A0A0U4X276. Mar. 16, 2016 (Year: 2016).*

Chen et al., "Coevolutionary Analysis Enabled Rational Deregulation of Allosteric Enzyme Inhibition in Corynebacterium glutamicum for Lysine Production," Applied and Environmental Microbiology, Jul. 2011, 77(13):4352-4360.

International Search Report and Written Opinion in International Appln. No. PCT/CN2021/117492, mailed on Dec. 8, 2021, 14 pages (submitted with English and machine translation).

Kalinowski et al., "Genetic and biochemical analysis of the aspartokinase from Corynebacterium glutamicum," Mol. Microbiol., May 1991, 5(5):1197-1204.

Liu et al., "Development of a CRISPR/Cas9 genome editing toolbox for Corynebacterium glutamicum," Microb. Cell Fact., Nov. 2017, 16(205), 17 pages.

Molecular Biology of the Gene, Fourth Ed., Dec. 1986, Chapter 8, p. 224.

(Continued)

*Primary Examiner* — Christian L Fronda
(74) *Attorney, Agent, or Firm* — Fish & Richardson P.C.

(57) ABSTRACT

Provided are a polypeptide with aspartate kinase activity and the use thereof in the production of an amino acid. Specifically, provided are a novel polypeptide with aspartate kinase activity, a recombinant polypeptide, a polynucleotide, a nucleic acid construct, a recombinant expression vector, a recombinant host cell, and a method for producing an amino acid. The polypeptide with aspartate kinase activity is a mutant mutated at one or more positions corresponding to positions 293, 294 and 307 of the amino acid sequence as shown in SEQ ID NO: 1. Compared with a polypeptide having the sequence as shown in SEQ ID NO: 1, the mutant polypeptide removes the feedback inhibition of lysine on aspartate kinase, has high aspartate kinase activity, and can be used for the stable and efficient production of lysine and derivatives thereof.

11 Claims, 1 Drawing Sheet

Specification includes a Sequence Listing.

(56) References Cited

OTHER PUBLICATIONS

Ruan et al., "Improving the electro-transformation efficiency of Corynebacterium glutamicum by weakening its cell wall and increasing the cytoplasmic membrane fluidity," Biotechnol. Lett., Sep. 2015, 37:2445-2452.

Stadtman et al., "Feed-back Inhibition and Repression of Aspartokinase Activity in *Escherichia coli* and *Saccharomyces cerevisiae*," Journal of Biological Chemistry, Jul. 1961, 236(7):2033-2038.

Wang et al., "Expanding targeting scope, editing window, and base transition capability of base editing in Corynebacterium glutamicum," Biotechnology and Bioengineering, Jul. 2019, 116(11):3016-3029.

Xu et al., "Aspartokinase G359D from Corynebacterium glutamicum Relieves the Synergistic Inhibition of Lysine and Threonine," Biotechnology Bulletin, Nov. 2017, 33(11):143-152.

* cited by examiner

SEQUENCE LISTING

```
<160> NUMBER OF SEQ ID NOS: 50

<210> SEQ ID NO 1
<211> LENGTH: 421
<212> TYPE: PRT
<213> ORGANISM: Corynebacterium glutamicum

<400> SEQUENCE: 1

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
```

```
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420


<210> SEQ ID NO 2
<211> LENGTH: 1266
<212> TYPE: DNA
<213> ORGANISM: Artificial Sequence
<220> FEATURE:
<223> OTHER INFORMATION: LysC gene sequence

<400> SEQUENCE: 2

gtggccctgg tcgtacagaa atatggcggt tcctcgcttg agagtgcgga acgcattaga     60

aacgtcgctg aacggatcgt tgccaccaag aaggctggaa atgatgtcgt ggttgtctgc    120

tccgcaatgg gagacaccac ggatgaactt ctagaacttg cagcggcagt gaatcccgtt    180

ccgccagctc gtgaaatgga tatgctcctg actgctggtg agcgtatttc taacgctctc    240

gtcgccatgg ctattgagtc ccttggcgca gaagcccaat ctttcacggg ctctcaggct    300

ggtgtgctca ccaccgagcg ccacggaaac gcacgcattg ttgatgtcac tccaggtcgt    360

gtgcgtgaag cactcgatga gggcaagatc tgcattgttg ctggtttcca gggtgttaat    420

aaagaaaccc gcgatgtcac cacgttgggt cgtggtggtt ctgacaccac tgcagttgcg    480

ttggcagctg ctttgaacgc tgatgtgtgt gagatttact cggacgttga cggtgtgtat    540

accgctgacc cgcgcatcgt tcctaatgca cagaagctgg aaaagctcag cttcgaagaa    600

atgctggaac ttgctgctgt tggctccaag attttggtgc tgcgcagtgt tgaatacgct    660

cgtgcattca atgtgccact tcgcgtacgc tcgtcttata gtaatgatcc cggcactttg    720

attgccggct ctatggagga tattcctgtg gaagaagcag tccttaccgg tgtcgcaacc    780

gacaagtccg aagccaaagt aaccgttctg ggtatttccg ataagccagg cgaggctgcg    840

aaggttttcc gtgcgttggc tgatgcagaa atcaacattg acatggttct gcagaacgtc    900

tcttctgtag aagacggcac caccgacatc accttcacct gccctcgttc cgacggccgc    960

cgcgcgatgg agatcttgaa gaagcttcag gttcagggca actggaccaa tgtgctttac   1020

gacgaccagg tcggcaaagt ctccctcgtg ggtgctggca tgaagtctca cccaggtgtt   1080

accgcagagt tcatggaagc tctgcgcgat gtcaacgtga acatcgaatt gatttccacc   1140
```

tctgagattc gtatttccgt gctgatccgt gaagatgatc tggatgctgc tgcacgtgca 1200
ttgcatgagc agttccagct gggcggcgaa gacgaagccg tcgtttatgc aggcaccgga 1260
cgctaa 1266

<210> SEQ ID NO 3
<211> LENGTH: 11773
<212> TYPE: DNA
<213> ORGANISM: Artificial Sequence
<220> FEATURE:
<223> OTHER INFORMATION: Plasmid sequence

<400> SEQUENCE: 3
aattaagctt aaaggcaccc gatatggata agaaatactc aataggctta gatatcggca 60
caaatagcgt cggatgggcg gtgatcactg atgaatataa ggttccgtct aaaaagttca 120
aggttctggg aaatacagac cgccacagta tcaaaaaaaa tcttataggg gctcttttat 180
ttgacagtgg agagacagcg gaagcgactc gtctcaaacg gacagctcgt agaaggtata 240
cacgtcggaa gaatcgtatt tgttatctac aggagatttt ttcaaatgag atggcgaaag 300
tagatgatag tttctttcat cgacttgaag agtctttttt ggtggaagaa gacaagaagc 360
atgaacgtca tcctattttt ggaaatatag tagatgaagt tgcttatcat gagaaatatc 420
caactatcta tcatctgcga aaaaaattgg tagattctac tgataaagcg gatttgcgct 480
taatctattt ggccttagcg catatgatta agtttcgtgg tcattttttg attgagggag 540
atttaaatcc tgataatagt gatgtggaca aactatttat ccagttggta caaacctaca 600
atcaattatt tgaagaaaac cctattaacg caagtggagt agatgctaaa gcgattcttt 660
ctgcacgatt gagtaaatca agacgattag aaaatctcat tgctcagctc cccggtgaga 720
agaaaaatgg cttatttggg aatctcattg ctttgtcatt gggtttgacc cctaatttta 780
aatcaaattt tgatttggca gaagatgcta aattacagct ttcaaaagat acttacgatg 840
atgatttaga taatttattg gcgcaaattg gagatcaata tgctgatttg tttttggcag 900
ctaagaattt atcagatgct attttacttt cagatatcct aagagtaaat actgaaataa 960
ctaaggctcc cctatcagct tcaatgatta aacgctacga tgaacatcat caagacttga 1020
ctcttttaaa agctttagtt cgacaacaac ttccagaaaa gtataaagaa atcttttttg 1080
atcaatcaaa aaacggatat gcaggttata ttgatggggg agctagccaa gaagaatttt 1140
ataaatttat caaaccaatt ttagaaaaaa tggatggtac tgaggaatta ttggtgaaac 1200
taaatcgtga agatttgctg cgcaagcaac ggacctttga caacggctct attccccatc 1260
aaattcactt gggtgagctg catgctattt tgagaagaca agaagacttt tatccatttt 1320
taaaagacaa tcgtgagaag attgaaaaaa tcttgacttt tcgaattcct tattatgttg 1380
gtccattggc gcgtggcaat agtcgttttg catggatgac tcggaagtct gaagaaacaa 1440
ttaccccatg gaattttgaa gaagttgtcg ataaaggtgc ttcagctcaa tcatttattg 1500
aacgcatgac aaactttgat aaaaatcttc caaatgaaaa agtactacca aaacatagtt 1560
tgctttatga gtattttacg gtttataacg aattgacaaa ggtcaaatat gttactgaag 1620
gaatgcgaaa accagcattt ctttcaggtg aacagaagaa agccattgtt gatttactct 1680
tcaaaacaaa tcgaaaagta accgttaagc aattaaaaga agattatttc aaaaaaatag 1740
aatgttttga tagtgttgaa atttcaggag ttgaagatag atttaatgct tcattaggta 1800
cctaccatga tttgctaaaa attattaaag ataaagattt tttggataat gaagaaaatg 1860

-continued

```
aagatatctt agaggatatt gttttaacat tgaccttatt tgaagatagg gagatgattg   1920
aggaaagact taaaacatat gctcacctct ttgatgataa ggtgatgaaa cagcttaaac   1980
gtcgccgtta tactggttgg ggacgtttgt ctcgaaaatt gattaatggt attagggata   2040
agcaatctgg caaaacaata ttagattttt tgaaatcaga tggttttgcc aatcgcaatt   2100
ttatgcagct gatccatgat gatagtttga catttaaaga agacattcaa aaagcacaag   2160
tgtctggaca aggcgatagt ttacatgaac atattgcaaa tttagctggt agccctgcta   2220
ttaaaaaagg tattttacag actgtaaaag ttgttgatga attggtcaaa gtaatggggc   2280
ggcataagcc agaaaatatc gttattgaaa tggcacgtga aaatcagaca actcaaaagg   2340
gccagaaaaa ttcgcgagag cgtatgaaac gaatcgaaga aggtatcaaa gaattaggaa   2400
gtcagattct taaagagcat cctgttgaaa atactcaatt gcaaaatgaa aagctctatc   2460
tctattatct ccaaaatgga agagacatgt atgtggacca agaattagat attaatcgtt   2520
taagtgatta tgatgtcgat cacattgttc cacaaagttt ccttaaagac gattcaatag   2580
acaataaggt cttaacgcgt tctgataaaa atcgtggtaa atcggataac gttccaagtg   2640
aagaagtagt caaaaagatg aaaaactatt ggagacaact tctaaacgcc aagttaatca   2700
ctcaacgtaa gtttgataat ttaacgaaag ctgaacgtgg aggtttgagt gaacttgata   2760
aagctggttt tatcaaacgc caattggttg aaactcgcca aatcactaag catgtggcac   2820
aaattttgga tagtcgcatg aatactaaat acgatgaaaa tgataaactt attcgagagg   2880
ttaaagtgat taccttaaaa tctaaattag tttctgactt ccgaaaagat ttccaattct   2940
ataaagtacg tgagattaac aattaccatc atgcccatga tgcgtatcta aatgccgtcg   3000
ttggaactgc tttgattaag aaatatccaa aacttgaatc ggagtttgtc tatggtgatt   3060
ataaagttta tgatgttcgt aaaatgattg ctaagtctga gcaagaaata ggcaaagcaa   3120
ccgcaaaata tttcttttac tctaatatca tgaacttctt caaaacagaa attacacttg   3180
caaatggaga gattcgcaaa cgccctctaa tcgaaactaa tggggaaact ggagaaattg   3240
tctgggataa agggcgagat tttgccacag tgcgcaaagt attgtccatg ccccaagtca   3300
atattgtcaa gaaaacagaa gtacagacag gcggattctc caaggagtca attttaccaa   3360
aaagaaattc ggacaagctt attgctcgta aaaaagactg ggatccaaaa aaatatggtg   3420
gttttgatag tccaacggta gcttattcag tcctagtggt tgctaaggtg gaaaaaggga   3480
aatcgaagaa gttaaaatcc gttaaagagt tactagggat cacaattatg gaaagaagtt   3540
cctttgaaaa aaatccgatt gactttttag aagctaaagg atataaggaa gttaaaaaag   3600
acttaatcat taaactacct aaatatagtc tttttgagtt agaaaacggt cgtaaacgga   3660
tgctggctag tgccggagaa ttacaaaaag gaaatgagct ggctctgcca agcaaatatg   3720
tgaatttttt atatttagct agtcattatg aaaagttgaa gggtagtcca gaagataacg   3780
aacaaaaaca attgtttgtg gagcagcata agcattattt agatgagatt attgagcaaa   3840
tcagtgaatt ttctaagcgt gttattttag cagatgccaa tttagataaa gttcttagtg   3900
catataacaa acatagagac aaaccaatac gtgaacaagc agaaaatatt attcatttat   3960
ttacgttgac gaatcttgga gctcccgctg cttttaaata ttttgataca acaattgatc   4020
gtaaacgata tacgtctaca aaagaagttt tagatgccac tcttatccat caatccatca   4080
ctggtcttta tgaaacacgc attgatttga gtcagctagg aggtgactga agcttggctg   4140
ttttggcgga tgagagaaga ttttcagcct gatacagatt aaatcagaac gcagaagcgg   4200
tctgataaaa cagaatttgc ctggcggcag tagcgcggtg gtcccacctg accccatgcc   4260
```

```
gaactcagaa gtgaaacgcc gtagcgccga tggtagtgtg gggtctgccc atgcgagagt   4320
agggaactgc caggcatcaa ataaaacgaa aggctcagtc gaaagactgg gcctttcgtt   4380
ttatctgttg tttgtcggtg aacgctctcc tgagtaggac aaatccgccg ggagcggatt   4440
tgaacgttgc gaagcaacgg cccggagggt ggcgggcagg acgcccgcca taaactgcca   4500
ggcatcaaat taagcagaag gccatcctga cggatggcct ttttgcgttt ctacaaactc   4560
ttttgtttat ttttctaaat acattcaaat atgtatccgc tcatgagaca ataaccctga   4620
taaatgcttc aataatattg aaaaaggaag agtatgagta ttcaacattt ccgtgtcgcc   4680
cttattccct tttttgcggc attttgcctt cctgtttttg ctcacccaga aacgctggtg   4740
aaagtaaaag atgctgaaga tcagttgggt gcacgagtgg gttacatcga actggatctc   4800
aacagcggta agatccttga gagttttcgc cccgaagaac gttttccaat gatgagcact   4860
tttgcttcct cgctcactga ctcgctgcgc tcggtcgttc ggctgcggcg agcggtatca   4920
gctcactcaa aggcggtaat acggttatcc acagaatcag gggataacgc aggaaagaac   4980
atgtgagcaa aaggccagca aaaggccagg aaccgtaaaa aggccgcgtt gctggcgttt   5040
ttccataggc tccgcccccc tgacgagcat cacaaaaatc gacgctcaag tcagaggtgg   5100
cgaaacccga caggactata aagataccag gcgtttcccc ctggaagctc cctcgtgcgc   5160
tctcctgttc cgaccctgcc gcttaccgga tacctgtccg cctttctccc ttcgggaagc   5220
gtggcgcttt ctcaatgctc acgctgtagg tatctcagtt cggtgtaggt cgttcgctcc   5280
aagctgggct gtgtgcacga accccccgtt cagcccgacc gctgcgcctt atccggtaac   5340
tatcgtcttg agtccaaccc ggtaagacac gacttatcgc cactggcagc agccactggt   5400
aacaggatta gcagagcgag gtatgtaggc ggtgctacag agttcttgaa gtggtggcct   5460
aactacggct acactagaag gacagtattt ggtatctgcg ctctgctgaa gccagttacc   5520
ttcggaaaaa gagttggtag ctcttgatcc ggcaaacaaa ccaccgctgg tagcggtggt   5580
ttttttgttt gcaagcagca gattacgcgc agaaaaaaag gatctcaaga agatcctttg   5640
atcttttcta cggggtctga cgctcagtgg aacgaaaact cacgttaagg gattttggtc   5700
atgagattat caaaaaggat cttcacctag atccttttgg ggtgggcgaa gaactccagc   5760
atgagatccc cgcgctggag gatcatccag ccattcgggg tcgttcactg gttccccttt   5820
ctgatttctg gcatagaaga acccccgtga actgtgtggt tccgggggtt gctgattttt   5880
gcgagacttc tcgcgcaatt ccctagctta ggtgaaaaca ccatgaaaca ctagggaaac   5940
acccatgaaa cacccattag ggcagtaggg cggcttcttc gtctagggct tgcatttggg   6000
cggtgatctg gtctttagcg tgtgaaagtg tgtcgtaggt ggcgtgctca atgcactcga   6060
acgtcacgtc atttaccggg tcacggtggg caaagagaac tagtgggtta gacattgttt   6120
tcctcgttgt cggtggtggt gagcttttct agccgctcgg taaacgcggc gatcatgaac   6180
tcttggaggt tttcaccgtt ctgcatgcct gcgcgcttca tgtcctcacg tagtgccaaa   6240
ggaacgcgtg cggtgaccac gacgggctta gcctttgcct gcgcttctag tgcttcgatg   6300
gtggcttgtg cctgcgcttg ctgcgcctgt agtgcctgtt gagcttcttg tagttgctgt   6360
tctagctgtg ccttggttgc catgctttaa gactctagta gctttcctgc gatatgtcat   6420
gcgcatgcgt agcaaacatt gtcctgcaac tcattcatta tgtgcagtgc tcctgttact   6480
agtcgtacat actcatattt acctagtctg catgcagtgc atgcacatgc agtcatgtcg   6540
tgctaatgtg taaaacatgt acatgcagat tgctgggggt gcagggggcg gagccaccct   6600
```

```
gtccatgcgg ggtgtggggc ttgccccgcc ggtacagaca gtgagcaccg gggcacctag   6660
tcgcggatac ccccccctagg tatcggacac gtaaccctcc catgtcgatg caaatcttta   6720
acattgagta cgggtaagct ggcacgcata gccaagctag gcggccacca aacaccacta   6780
aaaattaata gtccctagac aagacaaacc cccgtgcgag ctaccaactc atatgcacgg   6840
gggccacata acccgaaggg gtttcaattg acaaccatag cactagctaa gacaacgggc   6900
acaacacccg cacaaactcg cactgcgcaa ccccgcacaa catcgggtct aggtaacact   6960
gagtaacact gaaatagaag tgaacacctc taaggaaccg caggtcaatg agggttctaa   7020
ggtcactcgc gctagggcgt ggcgtaggca aaacgtcatg tacaagatca ccaatagtaa   7080
ggctctggcg gggtgccata ggtggcgcag ggacgaagct gttgcggtgt cctggtcgtc   7140
taacggtgct tcgcagtttg agggtctgca aaactctcac tctcgctggg ggtcatctct   7200
ggctgaattg gaagtcatgg gcgaacgccg cattgagctg gctattgcta ctaagaatca   7260
cttggcggcg ggtggcgcgc tcatgatgtt tgtgggcact gttcgacaca accgctcaca   7320
gtcatttgcg caggttgaag cgggtattaa gactgcgtac tcttcgatgg tgaaaacatc   7380
tcagtggaag aaagaacgtg cacggtacgg ggtggagcac acctatagtg actatgaggt   7440
cacagactct tgggcgaacg gttggcactt gcaccgcaac atgctgttgt tcttggatcg   7500
tccactgtct gacgatgaac tcaaggcgtt tgaggattcc atgttttccc gctggtctgc   7560
tggtgtggtt aaggccggta tggacgcgcc actgcgtgag cacggggtca aacttgatca   7620
ggtgtctacc tggggtggag acgctgcgaa aatggcaacc tacctcgcta agggcatgtc   7680
tcaggaactg actggctccg ctactaaaac cgcgtctaag ggtcgtaca cgccgtttca   7740
gatgttggat atgttggccg atcaaagcga cgccggcgag gatatggacg ctgttttggt   7800
ggctcggtgg cgtgagtatg aggttggttc taaaaacctg cgttcgtcct ggtcacgtgg   7860
ggctaagcgt gctttgggca ttgattacat agacgctgat gtacgtcgtg aaatggaaga   7920
agaactgtac aagctcgccg gtctggaagc accggaacgg gtcgaatcaa cccgcgttgc   7980
tgttgctttg gtgaagcccg atgattggaa actgattcag tctgatttcg cggttaggca   8040
gtacgttctc gattgcgtgg ataaggctaa ggacgtggcc gctgcgcaac gtgtcgctaa   8100
tgaggtgctg gcaagtctgg gtgtggattc caccccgtgc atgatcgtta tggatgatgt   8160
ggacttggac gcggttctgc ctactcatgg ggacgctact aagcgtgatc tgaatgcggc   8220
ggtgttcgcg ggtaatgagc agactattct tcgcacccac taaaagcggc ataaaccccg   8280
ttcgatattt tgtgcgatga atttatggtc aatgtcgcgg gggcaaacta tgatgggtct   8340
tgttgttggc gtcccggaaa acgattccga agcccaacct ttcatagaag gcggcggtgg   8400
aatttttctc cacataagct ggcaatgttg cgacgcaaca ggtacagtgt aattcatgag   8460
accacgcgtg gatccggctt actaaaagcc agataacagt atgcgtattt gcgcgctgat   8520
ttttgcggta taagaatata tactgatatg tatacccgaa gtatgtcaaa aagaggtatg   8580
ctatgaagca gcgtattaca gtgacagttg acagcgacag ctatcagttg ctcaaggcat   8640
atatgatgtc aatatctccg gtctggtaag cacaaccatg cagaatgaag cccgtcgtct   8700
gcgtgccgaa cgctggaaag cggaaaatca ggaagggatg gctgaggtcg cccggtttat   8760
tgaaatgaac ggctcttttg ctgacgagaa caggggctgg tgaaatgcag tttaaggttt   8820
acacctataa aagagagagc cgttatcgtc tgtttgtgga tgtacagagt gatattattg   8880
acacgcccgg gcgacggatg gtgatccccc tggccagtgc acgtctgctg tcagataaag   8940
tctcccgtga actttacccg gtggtgcata tcggggatga aagctggcgc atgatgacca   9000
```

ccgatatggc cagtgtgccg gtatccgtta tcggggaaga agtggctgat ctcagccacc 9060
gcgaaaatga catcaaaaac gccattaacc tgatgttctg ggaatataa ggtctcagtt 9120
ttagagctag aaatagcaag ttaaaataag gctagtccgt tatcaacttg aaaaagtggc 9180
accgagtcgg tgcttttttt ccaggcatca aataaaacga aaggctcagt cgaaagactg 9240
ggcctttcgt tttatctgtt gtttgtcggt gaacgctctc ctgagtagga caaatccgcc 9300
gggagcggat ttgaacgttg cgaagcaacg gcccggaggg tggcgggcag gacgcccgcc 9360
ataaactgcc aggcatcaaa ttaagcagaa ggccatcctg acggatggcc tttttgcgtt 9420
tctacaaact ctttttgttt atttttctaa atacattcaa atatgtatcc gctcatgaat 9480
taattccgct agatgacgtg cggcttcgaa aatctcgtga tggcaggttg ggcgtcgctt 9540
ggtcggtcat ttcgaagggc accaataact gccttaaaaa aattacgccc cgccctgcca 9600
ctcatcgcag tactgttgta attcattaag cattctgccg acatggaagc catcacagac 9660
ggcatgatga acctgaatcg ccagcggcat cagcaccttg tcgccttgcg tataatattt 9720
gcccatggtg aaaacggggg cgaagaagtt gtccatattg gccacgttta aatcaaaact 9780
ggtgaaactc acccagggat tggctgagac gaaaaacata ttctcaataa accctttagg 9840
gaaataggcc aggttttcac cgtaacacgc cacatcttgc gaatatatgt gtagaaactg 9900
ccggaaatcg tcgtggtatt cactccagag cgatgaaaac gtttcagttt gctcatggaa 9960
aacggtgtaa caagggtgaa cactatccca tatcaccagc tcaccgtctt tcattgccat 10020
acggaactcc ggatgagcat tcatcaggcg ggcaagaatg tgaataaagg ccggataaaa 10080
cttgtgctta tttttcttta cggtctttaa aaaggccgta atatccagct gaacggtctg 10140
gttataggta cattgagcaa ctgactgaaa tgcctcaaaa tgttctttac gatgccattg 10200
ggatatatca acggtggtat atccagtgat ttttttctcc attttagctt ccttagctcc 10260
tgaaaatctc gtcgaagctc ggcggatttg tcctactcaa gctgatccga caaaatccac 10320
acattatccc aggtgtccgg atcggtcaaa tacgctgcca gctcatagac cgtatccaaa 10380
gcatccgggg ctgatccccg gcgccagggt ggtttttctt ttcaccagtg agacgggcaa 10440
cagctgattg cccttcaccg cctggccctg agagagttgc agcaagcggt ccacgtggtt 10500
tgccccagca ggcgaaaatc ctgtttgatg gtggttaacg gcgggatata acatgagctg 10560
tcttcggtat cgtcgtatcc cactaccgag atatccgcac caacgcgcag cccggactcg 10620
gtaatggcgc gcattgcgcc cagcgccatc tgatcgttgg caaccagcat cgcagtggga 10680
acgatgccct cattcagcat ttgcatggtt tgttgaaaac cggacatggc actccagtcg 10740
ccttcccgtt ccgctatcgg ctgaatttga ttgcgagtga gatatttatg ccagccagcc 10800
agacgcagac gcgccgagac agaacttaat gggcccgcta acagcgcgat ttgctggtga 10860
cccaatgcga ccagatgctc cacgcccagt cgcgtaccgt cttcatggga gaaaataata 10920
ctgttgatgg gtgtctggtc agagacatca agaaataacg ccggaacatt agtgcaggca 10980
gcttccacag caatggcatc ctggtcatcc agcggatagt taatgatcag cccactgacg 11040
cgttgcgcga gaagattgtg caccgccgct ttacaggctt cgacgccgct tcgttctacc 11100
atcgacacca ccacgctggc acccagttga tcggcgcgag atttaatcgc cgcgacaatt 11160
tgcgacggcg cgtgcagggc cagactggag gtggcaacgc caatcagcaa cgactgtttg 11220
cccgccagtt gttgtgccac gcggttggga atgtaattca gctccgccat cgccgcttcc 11280
actttttccc gcgttttcgc agaaacgtgg ctggcctggt tcaccacgcg ggaaacggtc 11340

```
tgataagaga caccggcata ctctgcgaca tcgtataacg ttactggttt cacattcacc  11400

accctgaatt gactctcttc cgggcgctat catgccatac cgcgaaaggt tttgcaccat  11460

tcgatggtgt caacgtaaat gccgcttcgc cttcgcgcgc gaattgcaag ctgatccggg  11520

cttatcgact gcacggtgca ccaatgcttc tggcgtcagg cagccatcgg aagctgtggt  11580

atggctgtgc aggtcgtaaa tcactgcata attcgtgtcg ctcaaggcgc actcccgttc  11640

tggataatgt tttttgcgcc gacatcataa cggttctggc aaatattctg aaatgagctg  11700

ttgacaatta atcatcggct cgtataatgt gtggaattgt gagcgctcac aatttcacac  11760

aggaaacaga att                                                      11773


<210> SEQ ID NO 4
<211> LENGTH: 351
<212> TYPE: DNA
<213> ORGANISM: Corynebacterium glutamicum
<220> FEATURE:
<221> NAME/KEY: misc_feature
<222> LOCATION: (1)..(351)
<223> OTHER INFORMATION: Sequence of promoter mutant of ddh gene

<400> SEQUENCE: 4

gtgcgtggcg agttttacaa agaaccccac atcatcaatg cctaaatggc gggtattttc     60

atccaaaccc aaccgcgcat cattccaatg ctgatccacc ccatccggat aaaccaccat    120

gaacggcaac ggatcaaaag tcctgttggt gaagctgcgc cccacagatc ctgactgctg    180

ggagccatga aaatagatca gcgcatccgt ggtggaacca aaaggctcaa caatacgaaa    240

cgttcgcttt cggtcctgat gaaagagatg tccctgaatc atcatctaag tacaaaaggt    300

ggtaagctcg accaggacag tgccaccaca attttggagg attacaagaa c             351


<210> SEQ ID NO 5
<211> LENGTH: 5688
<212> TYPE: DNA
<213> ORGANISM: Artificial Sequence
<220> FEATURE:
<223> OTHER INFORMATION: Plasmid sequence

<400> SEQUENCE: 5

gtgcgtggcg agttttacaa agaaccccac atcatcaatg cctaaatggc gggtattttc     60

atccaaaccc aaccgcgcat cattccaatg ctgatccacc ccatccggat aaaccaccat    120

gaacggcaac ggatcaaaag tcctgttggt gaagctgcgc cccacagatc ctgactgctg    180

ggagccatga aaatagatca gcgcatccgt ggtggaacca aaaggctcaa caatacgaaa    240

cgttcgcttt cggtcctgat gaaagagatg tccctgaatc atcatctaag tacaaaaggt    300

ggtaagctcg accaggacag tgccaccaca attttggagg attacaagaa catgactaag    360

caaccaccaa tcgcaaaagc cgatctgcaa aaaactcagg gaaaccgtgc accagcagca    420

gttaaaaata gcgacgtgat tagttttatt aaccagccat caatgaaaga gcaactggca    480

gcagctcttc cacgccatat gacggctgaa cgtatgatcc gtatcgccac cacagaaatt    540

cgtaaagttc cggcgttagg aaactgtgac actatgagtt ttgtcagtgc gatcgtacag    600

tgttcacagc tcggacttga gccaggtagc gccctcggtc atgcatattt actgcctttt    660

ggtaataaaa acgaaaagag cggtaaaaag aacgttcagc taatcattgg ctatcgcggc    720

atgattgatc tggctcgccg ttctggtcaa atcgccagcc tgtcagcccg tgttgtccgt    780

gaaggtgacg agtttagctt cgaatttggc cttgatgaaa agttaataca ccgcccggga    840

gaaaacgaag atgccccggt tacccacgtc tatgctgtcg caagactgaa agacggaggt    900
```

-continued

```
actcagtttg aagttatgac gcgcaaacag attgagctgg tgcgcagcct gagtaaagct    960
ggtaataacg ggccgtgggt aactcactgg gaagaaatgg caaagaaaac ggctattcgt   1020
cgcctgttca aatatttgcc cgtatcaatt gagatccagc gtgcagtatc aatggatgaa   1080
aaggaaccac tgacaatcga tcctgcagat tcctctgtat taaccgggga atacagtgta   1140
atcgataatt cagaggaata actgttttgg cggatgagag aagattttca gcctgataca   1200
gattaaatca gaacgcagaa gcggtctgat aaaacagaat ttgcctggcg gcagtagcgc   1260
ggtggtccca cctgacccca tgccgaactc agaagtgaaa cgccgtagcg ccgatggtag   1320
tgtggggtct ccccatgcga gagtagggaa ctgccaggca tcaaataaaa cgaaaggctc   1380
agtcgaaaga ctgggccttt cgttttatct gttgtttgtc ggtgaacgct ctcctgagta   1440
ggacaaatcc gccgggagcg gatttgaacg ttgcgaagca acggcccgga gggtggcggg   1500
caggacgccc gccataaact gccaggcatc aaattaagca gaaggccatc ctgacggatg   1560
gcctttttgc gtttctacaa actcttttg tttattttc taaatacatt caaatatgta   1620
tccgctcatg aattaattcc gctagatgac gtgcggcttc gactagctcc aaaaaggtct   1680
ccaggatctc gaggagattt ttgaggggga gggagtcgag gaagagccag agcagaaggc   1740
ggggaaccgt tctctgccga cagcgtgagc ccccttaaa aatcaggccg gggaggaacc   1800
ggggagggat cagagctagg agcgagacac cctaaagggg gggaaccgtt ttctgctgac   1860
ggtgtttcgt ttattagttt tcagcccgtg gatagcggag ggtgagggca agtgagagcc   1920
agagcaagga cgggacccct aaaggggga accgttttct gctgacggtg tttcgtttat   1980
tagttttcag cccgtggacg gccgcgttta gcttccattc caagtgcctt tctgacttgt   2040
tggatgcgcc tttcactgac acctagttcg cctgcaagct cacgagtcga gggatcagca   2100
accgattgag aacgggcatc caggatcgca gttttgacgc gaagttcgag caactcgcct   2160
gtcatttctc ggcgtttgtt tgcttccgct aatcgctgtc gcgtctcctg cgcatactta   2220
ctttctgggt cagcccatct gcgtgcattc gatgtagctg cgccccgtcg ccccatcgtc   2280
gctagagctt tccgccctcg gctgctctgc gtttccaccc gacgagcagg gacgactggc   2340
tggcctttag ccacgtagcc gcgcacacga cgcgccatcg tcaggcgatc acgcatggcg   2400
ggaagatccg gctcccggcc gtctgcaccg accgcctggg caacgttgta cgccacttca   2460
tacgcgtcga tgatcttggc atcttttagg cgctcaccag cagctttgag ctggtatccc   2520
acggtcaacg cgtggcgaaa cgcggtctcg tcgcgcgctc gctctggatt tgtccagagc   2580
actcgcacgc cgtcgatcag gtcgccggac gcgtccaggg cgctcggcag gctcgcgtcc   2640
aaaatcgcta gcgccttggc ttctgcggtg gcgcgttgtg ccgcttcaat gcgggcgcgt   2700
ccgctggaaa agtcctgctc aatgtacttt ttcggcttct gtgatccggt catcgttcga   2760
gcaatctcca ttaggtcggc cagccgatcc acacgatcat gctggcagtg ccatttatag   2820
gctgtcggat cgtctgagac gtgcagcggc caccggctca gcctatgcga aaaagcctgg   2880
tcagcgccga aaacacgagt catttcttcc gtcgttgcag ccagcaggcg catatttggg   2940
ctggttttac ctgctgcggc atacaccggg tcaatgagcc agatgagctg gcatttcccg   3000
ctcagcggat tcacgccgat ccaagccggc gctttttcta ggcgtgccca tttctctaaa   3060
atcgcgtaga cctgcgggtt tacgtgctca atcttcccgc cggcctggtg gctgggcaca   3120
tcgatgtcaa gcacgatcac cgcggcatgt tgcgcgtgcg tcagcgcaac gtactggcac   3180
cgcgtcagcg cttttgagcc agcccggtag agctttggtt gggtttcgcc ggtatccggg   3240
```

-continued

```
tttttaatcc aggcgctcgc gaaatctctt gtcttgctgc cctggaagct ttcgcgtccc   3300
aggtgagcga gcagttcgcg gcgatcttct gccgtccagc cgcgtgagcc gcagcgcata   3360
gcttcggggt gggtgtcgaa cagatcggcg gacaatttcc acgcgctagc tgtgactgtg   3420
tcctgcggat cggctagagt catgtcttga gtgctttctc ccagctgatg actgggggtt   3480
agccgacgcc ctgtgagttc ccgctcacgg ggcgttcaac tttttcaggt atttgtgcag   3540
cttatcgtgt tttcttcgta aatgaacgct taactacctt gttaaacgtg gcaaataggc   3600
aggattgatg gggatctagc ttcacgctgc cgcaagcact cagggcgcaa gggctgctaa   3660
aggaagcgga acacgtagaa agccagtccg cagaaacggt gctgaccccg gatgaatgtc   3720
agctactggg ctatctggac aagggaaaac gcaagcgcaa agagaaagca ggtagcttgc   3780
agtgggctta catggcgata gctagactgg gcggttttat ggacagcaag cgaaccggaa   3840
ttgccagctg gggcgccctc tggtaaggtt gggaagccct gcaaagtaaa ctggatggct   3900
ttcttgccgc caaggatctg atggcgcagg ggatcaagat ctgatcaaga gacaggatga   3960
ggatcgtttc gcatgattga acaagatgga ttgcacgcag gttctccggc cgcttgggtg   4020
gagaggctat tcggctatga ctgggcacaa cagacaatcg gctgctctga tgccgccgtg   4080
ttccggctgt cagcgcaggg gcgcccggtt ctttttgtca agaccgacct gtccggtgcc   4140
ctgaatgaac tccaagacga ggcagcgcgg ctatcgtggc tggccacgac gggcgttcct   4200
tgcgcagctg tgctcgacgt tgtcactgaa gcgggaaggg actggctgct attgggcgaa   4260
gtgccggggc aggatctcct gtcatctcac cttgctcctg ccgagaaagt atccatcatg   4320
gctgatgcaa tgcggcggct gcatacgctt gatccggcta cctgcccatt cgaccaccaa   4380
gcgaaacatc gcatcgagcg agcacgtact cggatggaag ccggtcttgt cgatcaggat   4440
gatctggacg aagagcatca ggggctcgcg ccagccgaac tgttcgccag gctcaaggcg   4500
cggatgcccg acggcgagga tctcgtcgtg acccatggcg atgcctgctt gccgaatatc   4560
atggtggaaa atggccgctt ttctggattc atcgactgtg gccggctggg tgtggcggac   4620
cgctatcagg acatagcgtt ggctacccgt gatattgctg aagagcttgg cggcgaatgg   4680
gctgaccgct tcctcgtgct ttacggtatc gccgctcccg attcgcagcg catcgccttc   4740
tatcgccttc ttgacgagtt cttctgagcg ggactctggg gttcgcggaa tcatgaccaa   4800
aatcccttaa cgtgagtttt cgttccactg agcgtcagac cccgtagaaa agatcaaagg   4860
atcttcttga gatccttttt ttctgcgcgt aatctgctgc ttgcaaacaa aaaaaccacc   4920
gctaccagcg gtggtttgtt tgccggatca agagctacca actctttttc cgaaggtaac   4980
tggcttcagc agagcgcaga taccaaatac tgtccttcta gtgtagccgt agttaggcca   5040
ccacttcaag aactctgtag caccgcctac atacctcgct ctgctaatcc tgttaccagt   5100
ggctgctgcc agtggcgata agtcgtgtct taccgggttg gactcaagac gatagttacc   5160
ggataaggcg cagcggtcgg gctgaacggg gggttcgtgc acacagccca gcttggagcg   5220
aacgacctac accgaactga gatacctaca gcgtgagcta tgagaaagcg ccacgcttcc   5280
cgaagggaga aaggcggaca ggtatccggt aagcggcagg gtcggaacag gagagcgcac   5340
gagggagctt ccagggggaa acgcctggta tctttatagt cctgtcgggt ttcgccacct   5400
ctgacttgag cgtcgatttt tgtgatgctc gtcagggggg cggagcctat ggaaaaacgc   5460
cagcaacgcg gcctttttac ggttcctggc cttttgctgg ccttttgctc acatgttctt   5520
tcctgcgtta tcccctgatt ctgtggataa ccgtattacc gcctttgagt gagctgatac   5580
cgctcgccgc agccgaacga ccgagcgcag cgagtcagtg agcgaggaag cggaagagtg   5640
```

cctgatgcgg tattttctcc ttacgcatct gtgcggtatt tcacaccg 5688

<210> SEQ ID NO 6
<211> LENGTH: 78
<212> TYPE: DNA
<213> ORGANISM: Artificial Sequence
<220> FEATURE:
<223> OTHER INFORMATION: Primer sequence

<400> SEQUENCE: 6
gcgctcacaa tttcacacag gaaacagaat taattaagct taaaggcacc cgatatggat 60
aagaaatact caataggc 78

<210> SEQ ID NO 7
<211> LENGTH: 27
<212> TYPE: DNA
<213> ORGANISM: Artificial Sequence
<220> FEATURE:
<223> OTHER INFORMATION: Primer sequence

<400> SEQUENCE: 7
tcagtcacct cctagctgac tcaaatc 27

<210> SEQ ID NO 8
<211> LENGTH: 42
<212> TYPE: DNA
<213> ORGANISM: Artificial Sequence
<220> FEATURE:
<223> OTHER INFORMATION: Primer sequence

<400> SEQUENCE: 8
gtcagctagg aggtgactga agcttggctg ttttggcgga tg 42

<210> SEQ ID NO 9
<211> LENGTH: 30
<212> TYPE: DNA
<213> ORGANISM: Artificial Sequence
<220> FEATURE:
<223> OTHER INFORMATION: Primer sequence

<400> SEQUENCE: 9
ctgtgtgaaa ttgtgagcgc tcacaattcc 30

<210> SEQ ID NO 10
<211> LENGTH: 42
<212> TYPE: DNA
<213> ORGANISM: Artificial Sequence
<220> FEATURE:
<223> OTHER INFORMATION: Primer sequence

<400> SEQUENCE: 10
ctgtgcggta tttcacaccg gtgcgtggcg agttttacaa ag 42

<210> SEQ ID NO 11
<211> LENGTH: 82
<212> TYPE: DNA
<213> ORGANISM: Artificial Sequence
<220> FEATURE:
<223> OTHER INFORMATION: Primer sequence

<400> SEQUENCE: 11
gttcttgtaa tcctccaaaa ttgtggtggc actgtcctgg tcgagcttac cacctttttgt 60 acttagatga tgattcaggg ac 82

<210> SEQ ID NO 12
<211> LENGTH: 43
<212> TYPE: DNA
<213> ORGANISM: Artificial Sequence
<220> FEATURE:
<223> OTHER INFORMATION: Primer sequence

<400> SEQUENCE: 12
ttttggagga ttacaagaac atgactaagc aaccaccaat cgc 43

<210> SEQ ID NO 13
<211> LENGTH: 25
<212> TYPE: DNA
<213> ORGANISM: Artificial Sequence
<220> FEATURE:
<223> OTHER INFORMATION: Primer sequence

<400> SEQUENCE: 13
ttcctctgaa ttatcgatta cactg 25

<210> SEQ ID NO 14
<211> LENGTH: 45
<212> TYPE: DNA
<213> ORGANISM: Artificial Sequence
<220> FEATURE:
<223> OTHER INFORMATION: Primer sequence

<400> SEQUENCE: 14
taatcgataa ttcagaggaa taactgtttt ggcggatgag agaag 45

<210> SEQ ID NO 15
<211> LENGTH: 23
<212> TYPE: DNA
<213> ORGANISM: Artificial Sequence
<220> FEATURE:
<223> OTHER INFORMATION: Primer sequence

<400> SEQUENCE: 15
ggagaccttt ttggagctag tcg 23

<210> SEQ ID NO 16
<211> LENGTH: 23
<212> TYPE: DNA
<213> ORGANISM: Artificial Sequence
<220> FEATURE:
<223> OTHER INFORMATION: Primer sequence

<400> SEQUENCE: 16
ctagctccaa aaaggtctcc agg 23

<210> SEQ ID NO 17
<211> LENGTH: 23
<212> TYPE: DNA
<213> ORGANISM: Artificial Sequence
<220> FEATURE:
<223> OTHER INFORMATION: Primer sequence

<400> SEQUENCE: 17
cggtgtgaaa taccgcacag atg 23

<210> SEQ ID NO 18
<211> LENGTH: 24
<212> TYPE: DNA
<213> ORGANISM: Artificial Sequence
<220> FEATURE:
<223> OTHER INFORMATION: Primer sequence

<400> SEQUENCE: 18
ttcatgcaga aatcaacatt gaca 24

<210> SEQ ID NO 19
<211> LENGTH: 24
<212> TYPE: DNA
<213> ORGANISM: Artificial Sequence
<220> FEATURE:
<223> OTHER INFORMATION: Primer sequence

<400> SEQUENCE: 19
aaactgtcaa tgttgatttc tgca 24

<210> SEQ ID NO 20
<211> LENGTH: 24
<212> TYPE: DNA
<213> ORGANISM: Artificial Sequence
<220> FEATURE:
<223> OTHER INFORMATION: Primer sequence

<400> SEQUENCE: 20
ttcagcaggt gaaggtgatg tcgg 24

<210> SEQ ID NO 21
<211> LENGTH: 24
<212> TYPE: DNA
<213> ORGANISM: Artificial Sequence
<220> FEATURE:
<223> OTHER INFORMATION: Primer sequence

<400> SEQUENCE: 21
aaacccgaca tcaccttcac ctgc 24

<210> SEQ ID NO 22
<211> LENGTH: 90
<212> TYPE: DNA
<213> ORGANISM: Artificial Sequence
<220> FEATURE:
<223> OTHER INFORMATION: Primer sequence

<400> SEQUENCE: 22
ggtggtgccg tcttctacag aagagacgtt ctgcagaacc atgtcgargt tgatttctgc 60
atcagccaac gcacggaaaa ccttcgcagc 90

<210> SEQ ID NO 23
<211> LENGTH: 90
<212> TYPE: DNA
<213> ORGANISM: Artificial Sequence
<220> FEATURE:
<223> OTHER INFORMATION: Primer sequence

<400> SEQUENCE: 23
ggtggtgccg tcttctacag aagagacgtt ctgcagaacc atgtccwtgt tgatttctgc 60
atcagccaac gcacggaaaa ccttcgcagc 90

<210> SEQ ID NO 24
<211> LENGTH: 90
<212> TYPE: DNA
<213> ORGANISM: Artificial Sequence
<220> FEATURE:
<223> OTHER INFORMATION: Primer sequence

<400> SEQUENCE: 24
ggtggtgccg tcttctacag aagagacgtt ctgcagaacc atgtcgghgt tgatttctgc 60
atcagccaac gcacggaaaa ccttcgcagc 90

<210> SEQ ID NO 25
<211> LENGTH: 90
<212> TYPE: DNA
<213> ORGANISM: Artificial Sequence
<220> FEATURE:
<223> OTHER INFORMATION: Primer sequence

<400> SEQUENCE: 25
ggtggtgccg tcttctacag aagagacgtt ctgcagaacc atgtcgtdgt tgatttctgc 60
atcagccaac gcacggaaaa ccttcgcagc 90

<210> SEQ ID NO 26
<211> LENGTH: 90
<212> TYPE: DNA
<213> ORGANISM: Artificial Sequence
<220> FEATURE:
<223> OTHER INFORMATION: Primer sequence

<400> SEQUENCE: 26
ggtggtgccg tcttctacag aagagacgtt ctgcagaacc atgtctkggt tgatttctgc 60
atcagccaac gcacggaaaa ccttcgcagc 90

<210> SEQ ID NO 27
<211> LENGTH: 90
<212> TYPE: DNA
<213> ORGANISM: Artificial Sequence
<220> FEATURE:
<223> OTHER INFORMATION: Primer sequence

<400> SEQUENCE: 27
ggtggtgccg tcttctacag aagagacgtt ctgcagaacc atgtcwtcgt tgatttctgc 60
atcagccaac gcacggaaaa ccttcgcagc 90

<210> SEQ ID NO 28
<211> LENGTH: 90
<212> TYPE: DNA
<213> ORGANISM: Artificial Sequence
<220> FEATURE:
<223> OTHER INFORMATION: Primer sequence

<400> SEQUENCE: 28
ggtggtgccg tcttctacag aagagacgtt ctgcagaacc atgtcgcvgt tgatttctgc 60
atcagccaac gcacggaaaa ccttcgcagc 90

<210> SEQ ID NO 29
<211> LENGTH: 90
<212> TYPE: DNA
<213> ORGANISM: Artificial Sequence
<220> FEATURE:
<223> OTHER INFORMATION: Primer sequence

<400> SEQUENCE: 29
ggtggtgccg tcttctacag aagagacgtt ctgcagaacc atgtcgacgt tgatttctgc 60
atcagccaac gcacggaaaa ccttcgcagc 90

<210> SEQ ID NO 30
<211> LENGTH: 90
<212> TYPE: DNA
<213> ORGANISM: Artificial Sequence
<220> FEATURE:
<223> OTHER INFORMATION: Primer sequence

<400> SEQUENCE: 30
ggtggtgccg tcttctacag aagagacgtt ctgcagaacc atgtcccagt tgatttctgc 60
atcagccaac gcacggaaaa ccttcgcagc 90

<210> SEQ ID NO 31
<211> LENGTH: 90
<212> TYPE: DNA
<213> ORGANISM: Artificial Sequence
<220> FEATURE:
<223> OTHER INFORMATION: Primer sequence

<400> SEQUENCE: 31
gtcggtggtg ccgtcttcta cagaagagac gttctgcaga accatgadaa tgttgatttc 60
tgcatcagcc aacgcacgga aaaccttcgc 90

<210> SEQ ID NO 32
<211> LENGTH: 90
<212> TYPE: DNA
<213> ORGANISM: Artificial Sequence
<220> FEATURE:
<223> OTHER INFORMATION: Primer sequence

<400> SEQUENCE: 32
gtcggtggtg ccgtcttcta cagaagagac gttctgcaga accatcwtaa tgttgatttc 60
tgcatcagcc aacgcacgga aaaccttcgc 90

<210> SEQ ID NO 33
<211> LENGTH: 90
<212> TYPE: DNA
<213> ORGANISM: Artificial Sequence
<220> FEATURE:
<223> OTHER INFORMATION: Primer sequence

<400> SEQUENCE: 33
gtcggtggtg ccgtcttcta cagaagagac gttctgcaga accatgghaa tgttgatttc 60
tgcatcagcc aacgcacgga aaaccttcgc 90

<210> SEQ ID NO 34
<211> LENGTH: 90
<212> TYPE: DNA
<213> ORGANISM: Artificial Sequence
<220> FEATURE:
<223> OTHER INFORMATION: Primer sequence

<400> SEQUENCE: 34
gtcggtggtg ccgtcttcta cagaagagac gttctgcaga accatgtdaa tgttgatttc 60
tgcatcagcc aacgcacgga aaaccttcgc 90

<210> SEQ ID NO 35
<211> LENGTH: 90
<212> TYPE: DNA
<213> ORGANISM: Artificial Sequence
<220> FEATURE:
<223> OTHER INFORMATION: Primer sequence

<400> SEQUENCE: 35
gtcggtggtg ccgtcttcta cagaagagac gttctgcaga accattkgaa tgttgatttc 60
tgcatcagcc aacgcacgga aaaccttcgc 90

<210> SEQ ID NO 36
<211> LENGTH: 90
<212> TYPE: DNA
<213> ORGANISM: Artificial Sequence
<220> FEATURE:
<223> OTHER INFORMATION: Primer sequence

<400> SEQUENCE: 36
gtcggtggtg ccgtcttcta cagaagagac gttctgcaga accatttcaa tgttgatttc 60
tgcatcagcc aacgcacgga aaaccttcgc 90

<210> SEQ ID NO 37
<211> LENGTH: 90
<212> TYPE: DNA
<213> ORGANISM: Artificial Sequence
<220> FEATURE:
<223> OTHER INFORMATION: Primer sequence

<400> SEQUENCE: 37
gtcggtggtg ccgtcttcta cagaagagac gttctgcaga accatgcvaa tgttgatttc 60
tgcatcagcc aacgcacgga aaaccttcgc 90

<210> SEQ ID NO 38
<211> LENGTH: 90
<212> TYPE: DNA
<213> ORGANISM: Artificial Sequence
<220> FEATURE:
<223> OTHER INFORMATION: Primer sequence

<400> SEQUENCE: 38
gtcggtggtg ccgtcttcta cagaagagac gttctgcaga accatgacaa tgttgatttc 60
tgcatcagcc aacgcacgga aaaccttcgc 90

<210> SEQ ID NO 39
<211> LENGTH: 90
<212> TYPE: DNA
<213> ORGANISM: Artificial Sequence
<220> FEATURE:
<223> OTHER INFORMATION: Primer sequence

<400> SEQUENCE: 39
gtcggtggtg ccgtcttcta cagaagagac gttctgcaga accatccaaa tgttgatttc 60
tgcatcagcc aacgcacgga aaaccttcgc 90

<210> SEQ ID NO 40
<211> LENGTH: 90
<212> TYPE: DNA
<213> ORGANISM: Artificial Sequence
<220> FEATURE:
<223> OTHER INFORMATION: Primer sequence

<400> SEQUENCE: 40
cgcgcggcgg ccgtcggaac gagggcaggt gaaggtgatg tcggtgadgc cgtcttctac 60
agaagagacg ttctgcagaa ccatgtcaat 90

<210> SEQ ID NO 41
<211> LENGTH: 90
<212> TYPE: DNA
<213> ORGANISM: Artificial Sequence
<220> FEATURE:
<223> OTHER INFORMATION: Primer sequence

<400> SEQUENCE: 41
cgcgcggcgg ccgtcggaac gagggcaggt gaaggtgatg tcggtcwtgc cgtcttctac 60
agaagagacg ttctgcagaa ccatgtcaat 90

<210> SEQ ID NO 42
<211> LENGTH: 90
<212> TYPE: DNA
<213> ORGANISM: Artificial Sequence
<220> FEATURE:
<223> OTHER INFORMATION: Primer sequence

<400> SEQUENCE: 42
cgcgcggcgg ccgtcggaac gagggcaggt gaaggtgatg tcggtagmgc cgtcttctac 60
agaagagacg ttctgcagaa ccatgtcaat 90

<210> SEQ ID NO 43
<211> LENGTH: 90
<212> TYPE: DNA
<213> ORGANISM: Artificial Sequence
<220> FEATURE:
<223> OTHER INFORMATION: Primer sequence

<400> SEQUENCE: 43
cgcgcggcgg ccgtcggaac gagggcaggt gaaggtgatg tcggtgtdgc cgtcttctac 60
agaagagacg ttctgcagaa ccatgtcaat 90

<210> SEQ ID NO 44
<211> LENGTH: 90
<212> TYPE: DNA
<213> ORGANISM: Artificial Sequence
<220> FEATURE:
<223> OTHER INFORMATION: Primer sequence

<400> SEQUENCE: 44
cgcgcggcgg ccgtcggaac gagggcaggt gaaggtgatg tcggttkggc cgtcttctac 60
agaagagacg ttctgcagaa ccatgtcaat 90

<210> SEQ ID NO 45
<211> LENGTH: 90
<212> TYPE: DNA
<213> ORGANISM: Artificial Sequence
<220> FEATURE:
<223> OTHER INFORMATION: Primer sequence

<400> SEQUENCE: 45
cgcgcggcgg ccgtcggaac gagggcaggt gaaggtgatg tcggtwtcgc cgtcttctac 60
agaagagacg ttctgcagaa ccatgtcaat 90

<210> SEQ ID NO 46
<211> LENGTH: 90
<212> TYPE: DNA
<213> ORGANISM: Artificial Sequence
<220> FEATURE:
<223> OTHER INFORMATION: Primer sequence

<400> SEQUENCE: 46
cgcgcggcgg ccgtcggaac gagggcaggt gaaggtgatg tcggtgcvgc cgtcttctac 60
agaagagacg ttctgcagaa ccatgtcaat 90

<210> SEQ ID NO 47
<211> LENGTH: 90
<212> TYPE: DNA

```
<213> ORGANISM: Artificial Sequence
<220> FEATURE:
<223> OTHER INFORMATION: Primer sequence

<400> SEQUENCE: 47

cgcgcggcgg ccgtcggaac gagggcaggt gaaggtgatg tcggtgacgc cgtcttctac     60

agaagagacg ttctgcagaa ccatgtcaat                                      90


<210> SEQ ID NO 48
<211> LENGTH: 90
<212> TYPE: DNA
<213> ORGANISM: Artificial Sequence
<220> FEATURE:
<223> OTHER INFORMATION: Primer sequence

<400> SEQUENCE: 48

cgcgcggcgg ccgtcggaac gagggcaggt gaaggtgatg tcggtccagc cgtcttctac     60

agaagagacg ttctgcagaa ccatgtcaat                                      90


<210> SEQ ID NO 49
<211> LENGTH: 22
<212> TYPE: DNA
<213> ORGANISM: Artificial Sequence
<220> FEATURE:
<223> OTHER INFORMATION: Primer sequence

<400> SEQUENCE: 49

cggacgttga cggtgtgtat ac                                              22


<210> SEQ ID NO 50
<211> LENGTH: 23
<212> TYPE: DNA
<213> ORGANISM: Artificial Sequence
<220> FEATURE:
<223> OTHER INFORMATION: Primer sequence

<400> SEQUENCE: 50

gcacggaaat acgaatctca gag                                             23
```

POLYPEPTIDE WITH ASPARTATE KINASE ACTIVITY AND USE THEREOF IN PRODUCTION OF AMINO ACID

CROSS-REFERENCE TO RELATED APPLICATIONS

This application is a U.S. National Phase application under 35 U.S.C. § 371 of International Patent Application No. PCT/CN2021/117492, filed on Sep. 9, 2021, which claims priority to Chinese Application No. 202011110184.9, filed on Oct. 16, 2020. The entire contents of the parent applications are hereby incorporated by reference.

SEQUENCE LISTING

This application contains a Sequence Listing that has been submitted electronically as an ASCII text file named "54397-0007US1_SL_ST25.txt." The ASCII text file, created on Mar. 28, 2023, is 40,270 bytes in size. The material in the ASCII text file is hereby incorporated by reference in its entirety.

TECHNICAL FIELD

The present disclosure relates to the field of molecular biology and bioengineering, in particular to a polypeptide with aspartate kinase activity, a recombinant polypeptide, a polynucleotide encoding the polypeptide or the recombinant polypeptide, a nucleic acid construct, a recombinant expression vector, a recombinant host cell, and a method for producing an amino acid.

BACKGROUND

Lysine, of which the chemical name is 2,6-diaminopimelic acid, is an essential amino acid for animals and human body. It functions to promote growth, enhance immunity, and improve the function of the central nervous tissues. Lysine includes three optical isomers, namely L-form (levorotatory), D-form (dextrorotatory), and DL form (racemic), of which only the L-form is biologically utilizable, and the commonly referred lysine is L-lysine. Lysine is known as the first limited amino acid because cereal, the staple food of human, has a low content of lysine, while lack of lysine could lead to protein metabolic dysfunction and adverse effect on growth; also, lysine is susceptible to damage during processing. Lysine has a very important position in pharmaceutics, health, food, animal feed and cosmetic industries.

By far, there are three methods for industrial production of lysine, namely proteolysis method, chemical synthesis method, and microbial fermentation method. Among them, the microbial fermentation method has the advantages of low cost, high production intensity, high specificity, and low environmental pollution, and therefore becomes the most widely applied method in the industrial production of lysine. *Corynebacterium* and *Escherichia* bacteria are widely used in the industrial production of lysine. For example, commonly used *Escherichia* is *Escherichia coli*, commonly used *Corynebacterium* includes *Corynebacterium glutamicum* of the *Corynebacterium* genus, *Brevibacterium flavum* of the *Brevibacterium* genus, and some species of *Arthrobacterium* and some species of *Microbacterium*. Because of its physiological superiority, *Corynebacterium glutamicum* has become the most important strain for production in the industry.

*Corynebacterium glutamicum* has two pathways for lysine biosynthesis, i.e., the dehydrogenase pathway and the succinylase pathway. Lysine synthesis by *Corynebacterium glutamicum* through the dehydrogenase pathway involves six enzymes catalyzing reactions: aspartate kinase (AK, encoded by lysC gene), aspartate semialdehyde dehydrogenase (ASADH, encoded by asd gene), dihydrodipicolinate synthase (DHDPS, encoded by dapA gene), dihydrodipicolinate reductase (DHDPR, encoded by dapB gene), diaminopimelate dehydrogenase (DAPDH, encoded by ddh gene), and diaminopimelate decarboxylase (DAPDC, encoded by lysA gene). Lysine synthesis by *Corynebacterium glutamicum* through the succinylase pathway further involves four enzymes for the synthesis of meso-diaminopimelic acid: tetrahydrodipicolinate succinylase (encoded by dapD gene), N-succinyldiaminopimelate aminotransferase (encoded by dapC gene), succinyl diaminopimelate deacylase (encoded by and diaminopimelate epimerase (encoded by dapF gene). The first step of the L-aspartic acid biosynthetic pathway by *Corynebacterium glutamicum* is aspartate kinase catalyzing L-aspartate to produce aspartate phosphatase, which is also the rate-limiting step in lysine production. The activity of aspartate kinase is inhibited by feedback from lysine [1]. Therefore, how to remove the feedback inhibition of aspartate kinase by lysine in the lysine biosynthetic pathway is of high significance for the selective breeding of high lysine producing strains.

Reference Document 1 discloses mutants of aspartate kinase insensitive to lysine inhibition. By random mutagenesis of the encoding gene of aspartate kinase III (Aspartate kinase III, AKIII) isolated from *Escherichia coli*, two AK III mutants removing the feedback inhibition are screened and obtained, respectively substituting isoleucine for threonine at position 352 (T3521) and substituting isoleucine for methionine at position 318 (M3181). Although the two m AK III mutants are capable of removing the feedback inhibition of lysine on aspartate kinase, they cannot result in high-yield lysine producing strains with significant increase of lysine yield due to their low lysine production efficiency.

Reference Document 2 discloses aspartate kinase mutants from *Corynebacterium glutamicum*, including 279T, A279V, S301F, T3081, S301Y, G345D, R320Q T311I, and S381F. These mutant AK III can remove the feedback inhibition of lysine on aspartate kinase, but vary dramatically in the efficiency of lysine production. T311I is a mutant reported to have the best performance in the application of lysine production and can significantly increase the lysine yield of the strains. To obtain a aspartate kinase mutant removing the feedback inhibition of lysine while achieving higher performance in lysine production is a problem urging to be solved by a person skilled in the art.

REFERENCE DOCUMENTS

Reference Document 1: EP1394257
Reference Document 2: EP1590463A2

SUMMARY

Problem to be Solved

In view of the problems in the prior art, such as the problem that aspartate kinase mutants cannot produce lysine in a stable and highly efficient manner, the present disclosure provides a polypeptide with aspartate kinase activity, which is a mutant of the wild-type aspartate kinase. Compared with the wild-type aspartate kinase, the mutant polypeptide according to the present disclosure removes the feedback inhibition of lysine on aspartate kinase, has high aspartate kinase activity, and can be used for the stable and efficient production of lysine.

Solution to the Problem (1) A polypeptide with aspartate kinase activity, wherein the polypeptide is selected from a group consisting of any one of (i) to (iv):
(i) a mutant of the polypeptide having the sequence as shown in SEQ ID NO: 1, compared with the sequence as shown in SEQ ID NO: 1, the mutant comprising a mutation at least at one or more positions corresponding to positions 293, 294, and 307 of the sequence as shown in SEQ ID NO: 1;
(ii) a polypeptide having at least 70%, at least 80%, or at least 90% sequence identity with the sequence as shown in (i) and not comprising the polypeptide having the sequence as shown in SEQ ID NO: 1;
(iii) a polypeptide encoded by a polynucleotide, the polynucleotide being hybridized with the polynucleotide as shown in (a) or (b) under very high stringent conditions:
(a) a polynucleotide encoding a polypeptide having the amino acid sequence as shown in (i);
(b) a full-length complementary polynucleotide of (a);
(iv) a fragment of the polypeptide as shown in (i), (ii), (iii), the fragment still having aspartate kinase activity.
(2) The polypeptide according to (1), wherein the polypeptide is a polypeptide comprising a mutation as shown in at least one group of (c) to (e) as follows:
(c) the amino acid at a position corresponding to position 293 of the sequence as shown in SEQ ID NO: 1 being mutated from isoleucine (I) to serine (S), glycine (G), glutamic acid (E), proline (P), tryptophan (W), tyrosine (Y), histidine (H), methionine (M), glutamine (Q), cysteine (C), or arginine (R);
(d) the amino acid at a position corresponding to position 294 of the sequence as shown in SEQ ID NO: 1 being mutated from aspartic acid (D) to tyrosine (Y), tryptophan (W), or phenylalanine (F);
(e) the amino acid at a position corresponding to position 307 of the sequence as shown in SEQ ID NO: 1 being mutated from threonine (T) to tyrosine (Y), glycine (G), or phenylalanine (F).(3) The polypeptide according to (1) or (2), wherein the polypeptide comprises deletion or addition at least one amino acid residue at N-terminus or C-terminus of the polypeptide having the sequence as shown in (i).
(4) A recombinant polypeptide comprising the polypeptide according to any one of (1) to (3) and an exogenous polypeptide fused to the polypeptide; optionally, the exogenous polypeptide comprising a tag polypeptide; preferably, the exogenous polypeptide comprising a tag polypeptide and a spacer polypeptide linking the tag polypeptide to the polypeptide with aspartate kinase activity.
(5) An isolated polynucleotide, comprising a nucleotide sequence encoding the polypeptide according to any one of (1) to (3), or comprising a nucleotide sequence encoding the recombinant polypeptide according to (4).
(6) A nucleic acid construct, comprising the polynucleotide according to (5), the polynucleotide is operably linked to one or more regulatory sequence, the regulatory sequence directs production of polypeptides in an expression host.
(7) A recombinant expression vector, comprising the polynucleotide according to (5), or the nucleic acid construct according to (6).
(8) A recombinant host cell, comprising the polypeptide according to any one of (1) to (3), the recombinant polypeptide according to (4), the polynucleotide according to (5), the nucleic acid construct according to (6), or the recombinant expression vector according to (7).
(9) The recombinant host cell according to (8), wherein the host cell is from genus *Corynebacterium*, genus *Brevibacterium*, genus *Arthrobacterium*, genus *Microbacterium*, or genus *Escherichia*; preferably, the host cell is *Corynebacterium glutamicum* or *Escherichia coli.*
(10) Use of the polypeptide according to any one of (1) to (3), the recombinant polypeptide according to (4), the polynucleotide according to (5), the nucleic acid construct according to (6), the recombinant expression vector according to (7), or the recombinant host cell according to (8) or (9) in production of an amino acid;
preferably, the amino acid being selected from lysine, threonine, isoleucine, and an amino acid derivative thereof, wherein the amino acid derivative includes at least one of pentanediamine, 5-aminovaleric acid, glutaric acid, and hydroxyisoleucine.
(11) A method for producing an amino acid, comprising steps of producing an amino acid using the polypeptide according to any one of (1) to (3), the recombinant polypeptide according to (4), the polynucleotide according to (5), the nucleic acid construct according to (6), the recombinant expression vector according to (7), or the recombinant host cell according to (8) or (9);
optionally, the method further comprising a step of purifying or isolating the amino acid;
preferably, the amino acid being selected from lysine, threonine, isoleucine, and an amino acid derivative thereof, wherein the amino acid derivative includes at least one of pentanediamine, 5-aminoglutaric acid, glutaric acid, and hydroxyisoleucine.

Effects

In some embodiments, the present disclosure discovers a mutant of the wild-type aspartate kinase. The mutant removes the feedback inhibition of lysine on aspartate kinase, has high aspartate kinase activity, and can significantly increase lysine yield when applied in lysine production and realize stable and highly efficient lysine production. Further, the aspartate kinase mutant according to the present disclosure is highly efficient in the production of threonine, isoleucine, as well as amino acid derivatives such as pentanediamine, 5-aminovaleric acid, glutaric acid, and hydroxyisoleucine.

In some embodiments, the recombinant polypeptide, the isolated polynucleotide, the nucleic acid construct, and the recombinant expression vector according to the present disclosure each includes or expresses the above-mentioned polypeptide with aspartate kinase activity, and are applicable in the production of lysine and derivatives thereof.

In some embodiments, the recombinant host cell, the polypeptide with aspartate kinase activity removing the feedback inhibition of lysine, and the recombinant host cell according to the present application can accumulate excessive lysine, thus are suitable for industrial production of lysine and derivatives thereof.

In some embodiments, by using the polypeptide with aspartate kinase activity, the recombinant polypeptide, or the recombinant host cell, the method for producing an amino acid according to the present disclosure could realize stable and highly efficient production of amino acid. When applied to amino acid production, the method of the present disclosure could obtain high yield of lysine, threonine, isoleucine, and derivatives thereof.

DETAILED DESCRIPTION

Definitions of Terms

Figure 1:
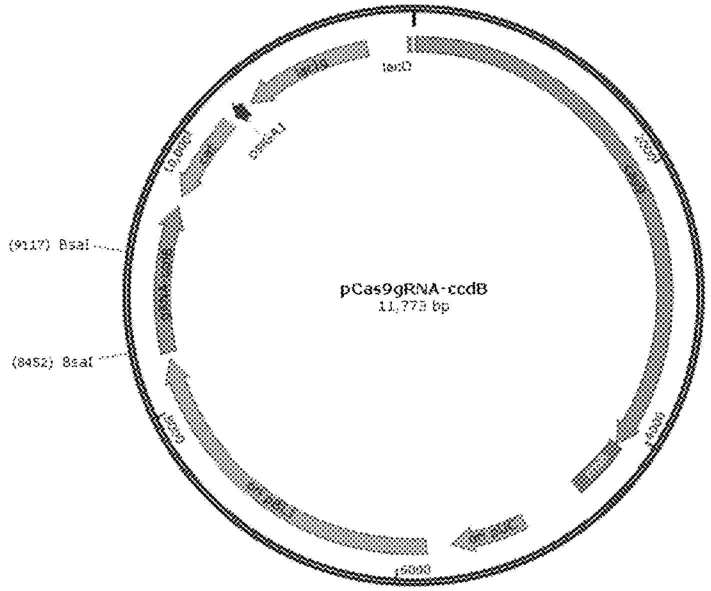
FIG. 1 shows a schematic diagram of pCas9gRNA-ccdB plasmid.

When used in combination with the term "including" in the claims and/or specification, the word "a" or "an" may refer to "one", or refer to "one or more", "at least one", and "one or more than one".

As used in the claims and specification, the term "including", "having", "comprising", or "containing" is intended to be inclusive or open-ended, and does not exclude additional or unrecited elements or methods and steps.

Throughout the application document, the term "about" means that a value includes the error or standard deviation caused by the device or method used to measure the value.

It is applicable to the content disclosed herein that the term "or" is defined only as alternatives and "and/or", but the term "or" used herein refers to "and/or" unless otherwise expressly stated to be only alternatives or mutual exclusion between alternatives.

The selected/optional/preferred "numerical range", when used in the claims or the specification, includes not only the numerical endpoints at both ends of the range, but also all natural numbers covered between the above numerical endpoints with respect to these numerical endpoints.

As used herein, although other organic or inorganic catalysis can be used, the term "converting" refers to chemical conversion from one molecule to another molecule catalyzed mainly by one or more polypeptides (enzymes); alternatively, the term may refer to a ratio (in %) of the molar mass of an expected product to the molar mass of a limiting substrate.

As used herein, the term "aspartate kinase" and its abbreviation "AK" refer to a polypeptide (enzyme) that can catalyze the phosphorylation of aspartic acid into an aspartyl phosphate. As the first key enzyme for the lysine biosynthetic pathway, aspartate kinase controls the biosynthetic pathway for the amino acids of the Aspartate family.

As used herein, the terms "polypeptide", "peptide", and "protein" are used interchangeably herein and are an amino acid polymer of any length. This polymer may be linear or branched. It may include modified amino acids, and can be spaced by non-amino acids. This term also includes amino acid polymers that have already been modified (e.g., by formation of disulfide bonds, glycosylation, lipidization, acetylation, phosphorylation, or any other manipulation such as conjugation with a labeled component).

As used herein, the term "fragment" means a polypeptide or a catalytic or carbohydrate-binding module having one or more (e.g., several) amino acids deleted from the amino terminus and/or the carboxyl terminus of a mature peptide or a domain. According to the present disclosure, the fragment has aspartate kinase activity.

As used herein, the term "wild-type" refers to an object that can be found in nature. For example, a polypeptide or a polynucleotide sequence present in an organism that can be isolated from a natural source and has not been intentionally modified by human in the laboratory is naturally occurring. As used herein, "naturally occurring" and "wild-type" are synonymous.

The term "mutant" used herein refers to a polynucleotide or polypeptide including alternation(s) (i.e., substitution, insertion and/or deletion) at one or more (e.g., several) positions, as compared with the "wild-type" or "comparative" polynucleotide or polypeptide. Here, substitution refers to a substitution of a different nucleotide or amino acid for a nucleotide or amino acid that occupies one position; deletion refers to removal of a nucleotide or amino acid that occupies some position; and insertion refers to an addition of a nucleotide or amino acid after the nucleotide or amino acid adjacent to and immediately following the occupied position. Exemplarily, the "mutant" of the present disclosure is a polypeptide with increased aspartate kinase activity.

As used herein, the term "amino acid mutation" or "nucleotide mutation" includes "substituting, repeating, deleting or adding one or more amino acid or nucleotide". In the present disclosure, the term "mutation" refers to a change in a nucleotide sequence or amino acid sequence. In a particular embodiment, the term "mutation" means "substitution".

In some embodiments, "mutation" according to the present disclosure includes the substitution of amino acids at one or more positions corresponding to positions 293, 294, and 307 of the sequence as shown in SEQ ID NO: 1. Compared with the polypeptide having the sequence as shown in SEQ ID NO: 1, the mutant with the amino acid substitution at the above positions removes the feedback inhibition of lysine on enzyme activity, and improves the conversion rate from aspartic acid to aspartyl phosphate, thereby increasing lysine production.

In the present disclosure, "mutation" also includes adding, deleting, or substituting amino acids at one or more positions corresponding to the sequence as shown in SEQ ID NO: 1 without affecting aspartate kinase activity. It is known that changing a few amino acid residues in some region of a polypeptide, such as in an non-essential region, would not substantially alter the biological activity. For example, a sequence obtained by appropriate substitution, addition or deletion of some amino acids will not have affected biological activity[2]. Exemplarily, the "mutation" of the present disclosure includes deletion or addition of at least one amino acid residue at a position corresponding to at least one of the C-terminus and the N-terminus of the polypeptide having the sequence as shown in SEQ ID NO: 1, and the mutant has aspartate kinase activity. In some embodiments, the "mutation" of the present disclosure includes deleting or adding, from the C-terminus or the N-terminus of the polypeptide having the sequence as shown in SEQ ID NO: 1, 1 to 20 amino acids, preferably 1 to 15 amino acids, more preferably 1 to 10 amino acids, more preferably 1 to 3 amino acids, and most preferably 1 amino acid, and the mutant has aspartate kinase activity.

In some embodiments, the "mutation" of the present disclosure may be selected from "conservative mutation". According to the present disclosure, the term "conservative mutation" refers to mutation that can maintain the normal function of proteins. A typical example of conservative mutation is conservative substitution.

As used herein, the term "conservative substitution" relates to substituting an amino acid residue for an amino acid residue having a similar side chain. The present field has defined amino acid residue families with similar side chains, including having basic side chains (e.g., lysine, arginine, and histidine), acid side chains (e.g., aspartic acid, glutamic acid), an uncharged polar side chain (e.g., glycine, asparagine, glutamine, serine, threonine, tyrosine, and cysteine), non-polar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine).

As used herein, "conservative substitution" typically involves the substitution of one amino acid at one or more positions of a protein. Such substitution may be conservative. As exemplary substitutions deemed as conservative substitution, examples include substitutions of Ala to Ser or Thr; substitutions of Arg to Gln, His or Lys; substitutions of Asn to Glu, Gln, Lys, His or Asp; substitutions of Asp to Asn, Glu or Gln; substitutions of Cys to Ser or Ala; substitutions of Gln to Asn, Glu, Lys, His, Asp or Arg; substitutions of Glu to Gly, Asn, Gln, Lys or Asp; substitutions of Gly to Pro; substitutions of His to Asn, Lys, Gln, Arg or Tyr; substitutions of Ile to Leu, Met, Val or Phe; substitutions of Leu to Ile, Met, Val or Phe; substitutions of Lys to Asn, Glu, Gln, His or Arg; substitutions of Met to Ile, Leu, Val or Phe; substitutions of Phe to Trp, Tyr, Met, Ile or Leu; substitutions of Ser to Thr or Ala; substitutions of Thr to Ser or Ala; substitutions of Trp to Phe or Tyr; substitutions of Tyr to His, Phe or Trp; and substitutions of Val to Met, Ile or Leu. In addition, conservative mutation also includes naturally occurring mutations that arise from individual differences, and the differences among strains or species, from which the genes originate.

As used herein, the term "recombinant polypeptide" refers to a fusion expression of two or more polypeptides by a genetic engineering approach. In some embodiments, the recombinant polypeptide is recombinant polypeptide obtained by fusing a mutant of a polypeptide having the sequence as shown in SEQ ID NO: 1 with an exogenous polypeptide. In some embodiments, the exogenous polypeptide comprises a tag polypeptide. In some embodiments, the exogenous polypeptide comprises a tag polypeptide, and a spacer polypeptide linking the mutant to the tag polypeptide. Specifically, the spacer polypeptide may have less than 10 spacer amino acid residues.

Exemplarily, the tag polypeptide is a polypeptide having the tag sequence as shown in Table 1.

TABLE 1

Tag Sequence

| Tag | Number of Residue | Sequence |
|---|---|---|
| Poly-Arg | 5 or 6 (typically 5) | RRRRR |
| Poly-His | 2 to 10 (typically 6) | HHHHHH |
| FLAG | 8 | DYKDDDDK |
| Strep-tag II | 8 | WSHPQFEK |
| c-myc | 10 | EQKLISEEDL |
| HA | 9 | YPYDVPDYA |

In some embodiments, the recombinant polypeptide comprises, from N-terminus to C-terminus: a mutant of a polypeptide having the sequence as shown in SEQ ID NO: 1, a spacer polypeptide, and a tag polypeptide; wherein the tag polypeptide may be a polypeptide having the tag sequence as shown in His6, the spacer polypeptide has less than 10 spacer amino acid residues. For example, the amino acid sequence of the spacer polypeptide is "LE".

As used herein, the term "sequence identity" or "identity percentage" in the comparison of two nucleic acids or polypeptides means that, when compared and aligned at maximum correspondence by the sequence alignment algorithm or by the visual inspection measurement, they are the same or they have a specific percentage of identical sequence measured. That is, the identity of nucleotide or amino acid residue sequences could be defined to be such a ratio that is a ratio of the number of nucleotides or amino acid residues that are identical to the total number of nucleotide or amino acid residues in the two or more nucleotides or amino acid residues aligned to have the maximum number of identical nucleotides or amino acid residues, with gaps introduced as needed.

The method for measuring "sequence identity" or "identity percentage" involved in the present disclosure includes, but not limited to: Lesk, A.M. (Ed.). (1988). *Computational Molecular Biology*. New York: Oxford University Press.; Smith, D. W. (Ed.). (1993). *Biocomputing Informatics and Genome Projects*. New York: Academic Press.; Griffin, A.M. & Griffin, H. G (Ed.). (1994). *Computer Analysis of Sequence Data, Part I*. New Jersey: Humana Press.; von Heinje G (1987). *Sequence Analysis in Molecular Biology*. Academic Press.; Gribskov, M. & Devereux, J. (Ed.). (1991) *Sequence Analysis Primer*. New York: M Stockton Press.; and Carillo, H. & Lipman, D., SIAM J. Applied Math. 48:1073 (1988). A preferable method for measuring identity requires obtaining maximum correspondence of sequence. The method for measuring identity is compiled in a computer program accessible by the public. The preferable computer-program method for measuring identity between two sequences includes, but not limited to: GCG program package (Devereux, J. et. al., 1984), BLASTP, BLASTN, and FASTA (Altschul, S. F. et. al., 1990). The public may acquire the BLASTX program from NCBI and other sources (Altschul, S. et. al. *BLAST Manual*. NCBI NLM NIH Bethesda, Md.20894; Altschul, S. et. al., 1990). The well-known Smith Waterman algorithm may also be used for measuring the identity.

In some embodiments, the polypeptide with aspartate kinase activity according to the present disclosure has at least 70%, 75%, 80%, 85%, 90%, 91%, 92%, 93%, 94%, 95%, 96%, 97%, 98% or 99% "sequence identity" or "identity percentage" of amino acid residues with the mutant of the polypeptide having the sequence as shown in SEQ ID NO: 1. In some other embodiments, the polynucleotide of the present disclosure for encoding the polypeptide with aspartate kinase activity has at least 70%, 75%, 80%, 85%, 90%, 91%, 92%, 93%, 94%, 95%, 96%, 97%, 98% or 99% "sequence identity" or "identity percentage" of nucleotide with the polynucleotide encoding the mutant of the polypeptide having the sequence as shown in SEQ ID NO: 1. Determination/calculation of the "sequence identity" or "identity percentage" may be based on any suitable region of the sequence, such as a region of a length of at least about 50 residues, at least about 100 residues, at least about 200 residues, at least about 400 residues, or at least about 500 residues. In some embodiments, the sequence is substantially identical at full length of any one or two biopolymers for comparison (e.g., nucleic acid or polypeptide).

As used herein, the term "polynucleotide" refers to a polymer composed of nucleotides. Polynucleotide can be in the form of a individual fragment or a component of a larger nucleotide sequence structure, and it is derived from a nucleotide sequence separated at least once in quantity or concentration and can be recognized, manipulated and restored from the sequence and its component nucleotide sequences by standard molecular biology methods (such as using a cloning vector). When a nucleotide sequence is represented by a DNA sequence (i.e., A, T, Q C), this also includes an RNA sequence (i.e., A, U, Q C), wherein "U" replaces "T". In other words, "polynucleotide" refers to a nucleotide polymer that has been removed from other nucleotides (an individual fragment or an entire fragment), or may be a constituent part or component of a larger nucleotide structure, such as an expression vector or a polycistronic sequence. The polynucleotide includes DNA, RNA and cDNA sequences.

As used herein, the term "isolated" refers to a substance in a form or environment that does not occur in nature. Non-limiting examples of isolated substances include (1) any substance that is not naturally occurring, (2) any substance including, but not limited to, any enzyme, mutant, nucleic acid, protein, peptide, or cofactor that is at least partially knocked out from one or more or all naturally occurring components associated with its nature; (3) any substance that is artificially modified relative to a naturally occurring substance; or (4) any substance that is modified by increasing the amount of the substance relative to other components associated with its nature (e.g., recombinant production in the host cell; multiple copies of the gene encoding the substance; and use of a promoter stronger than the promoter naturally associated with the gene encoding the substance). The isolated substance may be present in the fermentation broth sample. For example, host cells may be genetically modified to express the polypeptide of the present disclosure. The fermentation broth sample from the host cells will contain isolated polypeptides. The "recombinant polynucleotide" pertains to a "polynucleotide".

As used herein, the term "recombinant polynucleotide" refers to a polynucleotide having a sequence that is not linked together in nature. The recombinant polynucleotide may be included in a suitable vector that could be transformed to a suitable host cell. A host cell comprising a recombinant polynucleotide is referred to as a "recombinant host cell". Subsequently, the polynucleotide is expressed in the recombinant host cell to generate for example a "recombinant polypeptide".

As used herein, the term "expression" includes any step relating to the production of polypeptides, including, but not limited to: transcription, post-transcriptional modification, translation, post-translational modification, and secretion.

As used herein, the term "expression vector" refers to a linear or circular DNA molecule comprising a polynucleotide encoding a polypeptide, the polynucleotide effectively linked to a regulatory sequence for its expression.

As used herein, the term "recombinant expression vector" refers to a DNA structure for expressing for example a polynucleotide encoding the desired polypeptide. The recombinant expression vector may include, for example including i) a set of genetic elements regulating the gene expression, such as a promoter and a enhancer; ii) structures or coding sequences transcribed into mRNA and translated into proteins; and iii) transcriptional subunits that properly transcribes and translate the initiation and termination sequences. The recombinant expression vector may be constructed by any suitable method. The nature of the vector is not important; any vector may be used, including a plasmid, a virus, a phage, and a transposon. Possible vectors used in the present disclosure include, but not limited to, chromosomes, achromosomes, and synthesized DNA fragments, such as bacterial plasmid, phage DNAs, yeast plasmids, and vectors derived from a combination of plasmids and phage DNAs, virus DNAs from for example cowpox, adenovirus, fowl pox, baculovirus, SV40, and pseudorabies virus.

As used herein, the term "recombinant gene" refers to genes that are not naturally occurring. A recombinant gene includes a protein-coding sequence operably linked to an expression regulatory sequence. Examples include, but not limited to: exogenous genes introducing microbes, endogenous protein-coding sequences operably linked to a heterelogous promoter, and genes having a modified protein-coding sequence. Recombinant genes are stored in genomes of microbiomes, plasmids in microbiomes, or phages in microbiomes.

As used herein, the term "operably linked" refers to a construction in which a regulatory sequence is placed at a proper position with respect to the coding sequence of the polynucleotide such that the regulatory sequence guides the expression of the coding sequence. Exemplarily, the regulatory sequence may be selected from a promoter and/or enhancer-coding sequence.

As used herein, the term "nucleic acid construct" includes a polynucleotide effectively linked to a suitable regulatory sequence and encoding a polypeptide or a domain or a module, the regulatory sequence being necessary for the polynucleotide expression of the selected cells or strands. In the present disclosure, the transcriptional regulator comprises a promoter. Further, it may comprise an element such as an enhancer, a silencer, and an insulator.

The term "host cell" used herein refers to any type of cells that may be easily transformed, transfected, or transduced with a mutant polypeptide of the present disclosure, a polynucleotide encoding the mutant polypeptide or a recombinant expression vector. The term "recombinant host cell" covers a host cell that is different from the parent cells after introducing the polynucleotide encoding a mutant polypeptide or a recombinant expression vector. The host cell of the present disclosure may be a prokaryotic cell or a eukaryotic cell, as long as it is a cell into which a polynucleotide encoding the polypeptide and recombinant polypeptide with aspartate kinase activity of the present disclosure can be introduced. In an embodiment, the host cell refers to a prokaryotic cell. More specifically, the host cell is derived from microbiomes suitable for production of an amino acid by fermentation, such as genus *Corynebacterium*, genus *Brevibacterium*, genus *Microbacterium*, or genus *Escherichia. Preferably, the host cell is derived from Corynebacterium glutamicum* of genus *Corynebacterium*, or is derived from *Escherichia coli* of genus *Escherichia.*

The terms "transformation, transfection, transduction" used herein has the meaning generally understood by a person skilled in the art, i.e., a process of introducing an exogenous DNA into a host. Methods for transformation, transfection, and transduction include any method for introducing a nucleic acid into a cell. These methods include, but are not limited to, electroporation, calcium phosphate ($CaPO_4$) precipitation, calcium chloride ($CaCl_2$)) precipitation, microinjection, a polyethylene glycol (PEG) method, a DEAE-dextran method, a cationic liposome method, and a lithium acetate-DMSO method.

In the present disclosure, the host cells may be cultured by conventional methods in the art, including, but not limited to, well-plate culture, shaking culture, batch culture, continuous culture, fed batch culture, etc. Also, various culturing conditions such as temperature, time, and pH value of the medium may be properly adjusted according to actual situations.

As used herein, the term "high-stringent conditions" means that following the standard DNA blotting procedures, a probe of at least 100 nucleotides in length pre-hybridizes or hybridizes for 12 to 24 hours at 42° C. in 5×SSPE (saline sodium phosphate EDTA), 0.3% SDS, 200 μg/ml of cleaved and denatured salmon sperm DNA, and 50% formamide. Finally, the vector material is washed three times at 65° C. with 2×SSC and 0.2% SDS, each for 15 min.

As used herein, the term "very high-stringent conditions" means that following the standard DNA blotting procedures, a probe of at least 100 nucleotides in length pre-hybridizes or hybridizes for 12 to 24 hours at 42° C. in 5×SSPE (saline sodium phosphate EDTA), 0.3% SDS, 200 μg/ml of cleaved and denatured salmon sperm DNA, and 50% formamide. Finally, the vector material is washed three times at 70° C. with 2×SSC and 0.2% SDS, each for 15 min.

Unless otherwise defined or clearly specified in the background, all technical and scientific terms used herein have the same meanings as typically understood by one of ordinary skill in the art to which the present disclosure belongs.

Mutants of Aspartate Kinase

In some embodiments, the present disclosure constructed a library of LysC gene mutants encoding aspartate kinase in *Corynebacterium glutamicum* by site-directed mutagenesis. From the library, mutants that could remove the feedback inhibition of lysine and thereby increase aspartate kinase activity were screened.

In some embodiments of the present disclosure, the mutation positions of mutants removing the lysine feedback inhibition include amino acids substituted at one or more positions corresponding to positions 293, 294 and 307 of the sequence as shown in SEQ ID NO: 1.

Exemplarily, the mutation at position 293 includes an amino acid mutated from isoleucine (I) to serine (S), glycine (G), glutamic acid (E), proline (P), tryptophan (W), tyrosine (Y), histidine (H), methionine (M), glutamine (Q), cysteine (C), or arginine (R).

The mutation at position 294 includes an amino acid mutated from aspartic acid (D) to tyrosine (Y), tryptophan (W), phenylalanine (F).

The mutation at position 307 includes an amino acid mutated from threonine (T) to tyrosine (Y), glycine (G), phenylalanine (F).

In some embodiments, the present disclosure provides a polypeptide with aspartate kinase activity, having at least 70%, 75%, 80%, 85%, 90%, 91%, 92%, 93%, 94%, 95%, 96%, 97%, 98%, 99%, 100% sequence identity to the polypeptide having the sequence as shown in SEQ ID NO: 1, and having an amino acid sequence that is not SEQ ID NO: 1.

In some embodiments, the present disclosure provides a polypeptide with aspartate kinase activity, comprising addition or deletion of amino acids from at least one of the N-terminus and the C-terminus of the mutant of aspartate kinase.

In some particular embodiments, the mutant of aspartate kinase has deletion or addition of 1 to 20 amino acids, preferably 1 to 15 amino acids, more preferably 1 to 10 amino acids, more preferably 1 to 3 amino acids, and most preferably 1 amino acid, from at least one of the N-terminus and the C-terminus, and has aspartate kinase activity.

In some embodiments, the present disclosure provides a polynucleotide encoding the mutant of aspartate kinase, the polynucleotide encoding a mutant of a polypeptide having the sequence as shown in SEQ ID NO: 1. Specifically, the polynucleotide is a LysC gene mutant of high lysine production that is screened from the library of LysC gene mutants. The nucleotide sequence of LysC gene is as shown in SEQ ID NO: 2.

In some embodiments, the corresponding nucleotide sequence of the polynucleotide encoding the amino acid of position 293 is selected from any one of the following groups: TCC; GGC; GAA; CCA; TGG; TAC; CAC; ATG; CAA; TGC; CGC. Preferably, the corresponding nucleotide sequence of the polynucleotide encoding the amino acid of position 293 is selected from any one of the following groups: TCC; GGC; GAA; CCA; TGG; TAC; CAC; ATG; CAA.

In some embodiments, the corresponding nucleotide sequence of the polynucleotide encoding the amino acid of position 294 is selected from any one of the following groups: TAC; TGG; TTC. Preferably, the corresponding nucleotide sequence of the polynucleotide encoding the amino acid of position 294 is selected from any one of the following groups: TGG; TTC.

In some embodiments, the corresponding nucleotide sequence of the polynucleotide encoding the amino acid of position 307 is selected from any one of the following groups: TAC; GGC; TTC. Preferably, the corresponding nucleotide sequence of the polynucleotide encoding the amino acid of position 307 is selected from any one of the following groups: TAC; GGC.

Construction of the Library of LysC Gene Mutants

With the pCas9 plasmid[3] as a template and cas9-1/cas9-2 as amplification primers, an amplified fragment 1 comprising Cas9 was amplified, wherein operating element lacO mutation and RBS mutation were introduced into the primers cas9-1/cas9-2.

With pnCas9(D10A)-AID-gRNA-ccdB$^{TS}$ [4] as a template and gRNA-1/gRNA-2 as amplification primers, an amplified fragment 2 comprising a gRNA-ccdB expression cassette and a temperature sensitive replication origin was amplified.

The amplified fragment 1 and the amplified fragment 2 were recombinantly linked, obtaining the pCas9gRNA-ccdB plasmid. The obtained pCas9gRNA-ccdB plasmid had a plasmid vector map as shown in FIG. 1 and a sequence as shown in SEQ ID NO: 3.

With the *Corynebacterium glutamicum* ATCC13032 genome as a template and $P_{ddh}$-1/$P_{ddh}$-2 as primers, a promoter mutant comprising the ddh gene was amplified as an amplified fragment 3.

With the *Escherichia coli* MG1655 genome as a template and recT-1/recT-2 as primers, the recT gene was amplified as an amplified fragment 4.

With the pEC-XK99E plasmid as a template and rrnB-1/rrnB-2 as primers, the rrnB terminator was amplified as an amplified fragment 5.

With the pEC-XK99E plasmid as a template and PEC-1/PEC-2 as primers, a fragment of the plasmid skeleton from which the per gene was knocked out was amplified as an amplified fragment 6.

Figure 2:
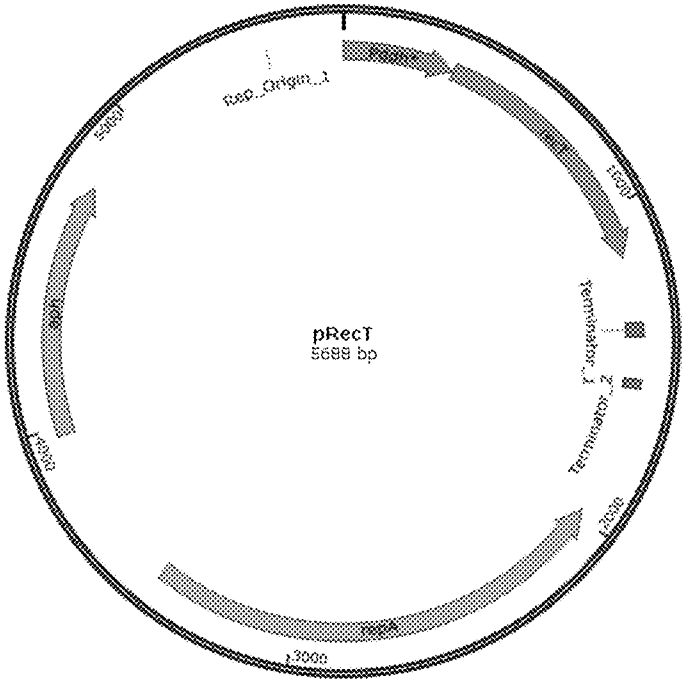
FIG. 2 shows a schematic diagram of pRecT plasmid.

The amplified fragment 3, the amplified fragment 4, the amplified fragment 5, and the amplified fragment 6 were recombinantly linked, obtaining the pRecT plasmid expressing RecT. The pRecT plasmid had a plasmid vector map as shown in FIG. 2 and a sequence as shown in SEQ ID NO: 5.

The pCas9gRNA plasmids respectively targeting positions 293/294 and 307 of lysC gene were constructed by Goldengate Cloning method, wherein the target DNA-binding region of gRNA-1 was TGCAGAAATCAACAT- TGACA, the target DNA-binding region of gRNA-2 was GCAGGTGAAGGTGATGTCGG Specifically, lysC-F1/lysC-R1, lysC-F2/lysC-R2 were denatured and annealed, and were then subjected to Goldengate Cloning together with the pCas9gRNA-ccdB plasmid, respectively, obtaining pCas9gRNA-lysC1 plasmid and pCas9gRNA-lysC2 plasmid.

The pRecT plasmid was electrotransformed into *Corynebacterium glutamicum* ATCC13032, obtaining the ATCC13032 (pRecT) strain. The single-stranded DNAs of 293-1 to 293-9, 294-1 to 294-9 and the single-stranded DNAs of 307-1 to 307-9 were designed respectively, as recombination templates for mutant construction. The pCas9gRNA-lysC1 plasmid and the single-stranded DNAs of 293-1 to 293-9, 294-1 to 294-9, and the pCas9gRNA-lysC2 plasmid and the single-stranded DNAs of 307-1 to 307-9 were respectively introduced into ATCC13032 (pRecT) competent cells. The competent cells transfected with the plasmids and single-stranded DNAs were coated on a plate, respectively. Monoclonal strains comprising amino acid mutations at positions 293, 294, 307 were screened, obtaining the library ofLysC gene mutants.

In some embodiments, the competent cells transfected with the target DNA were added into 1 mL TSB liquid medium pre-heated at 46° C., subjected to heat shock at 46° C. for 6 min, incubated at 30° C. for 3 h, coated on TSB plates supplemented with 5 µg/mL chloramphenicol and 0.05 mM IPTG and incubated for 2 days, to grow hundreds of clones which were screened to obtain a library of mutants at amino acid positions 293, 294, 307.

The ingredients (g/L) of the TSB liquid medium were as follows: glucose, 5 g/L; yeast powder, 5 g/L; soy peptone, 9 g/L; urea, 3 g/L; succinic acid, 0.5 g/L; $K_2HPO_4 \cdot 3H_2O$, 1 g/L; $MgSO_4 \cdot 7H_2O$, 0.1 g/L; biotin, 0.01 mg/L; vitamin B1, 0.1 mg/L; MOPS, 20 g/L. The solid medium was supplemented with 15 g/L agar powder.

The *Corynebacterium glutamicum* is specifically *Corynebacterium glutamicum* ATCC 13032 (*Corynebacterium glutamicum* ATCC 13032, Gene ID: 2830649).

Production Process of Amino Acids (1) Monoclonal strains with high lysine production were screened in the library of LysC gene mutants with amino acid mutations at positions 293, 294, 307 by a method that reproducibly yielded the screening results as recombinant host cells for amino acid production.

(2) The recombinant host cells were subjected to fermentation culture. Amino acids were collected from the recombinant host cells or the culture broth of the recombinant host cells, thereby completing the production of amino acids.

During the above production process of amino acids, the mutant LysC genes comprised by the recombinant host cells could encode the aspartate kinase removing lysine inhibition. The recombinant host cells could accumulate a huge amount of lysine, realizing stable and highly effective production of lysine, threonine, isoleucine, and derivatives thereof.

For the produced amino acids, the amino acids are selected from lysine, threonine, isoleucine, and an amino acid derivative thereof, wherein the amino acid derivative thereof includes at least one of pentanediamine, 5-aminovaleric acid, glutaric acid, and hydroxyisoleucine.

For the recombinant host cells, a recombinant host cell may also comprise other enzymes associated with synthesis of amino acids. Exemplarily, enzymes associated with synthesis of amino acids include a combination of one or two of: aspartate kinase, aspartate semialdehyde dehydrogenase, aspartate ammonia lyase, dihydrodipicolinate synthase, dihydrodipicolinate reductase, succinyl diaminopimelate aminotransferase, tetrahydrodipicolinate succinylase, succinyl diaminopimelate deacylase, diaminopimelic acid epimerase, diaminopimelic acid deacylase, glyceraldehyde-3-phosphate dehydrogenase, lysine transport protein, transketolase, diaminopimelate dehydrogenase, and pyruvate carboxylase.

In some embodiments, activity or expression of the enzyme associated with synthesis of amino acids may be enhanced by gene engineering, for example, by introducing strong promoters or by means of expression by free plasmids to increase the expression intensity of the genes encoding the enzymes associated with the synthesis of amino acids, or by chromosomal integration to integrate genes encoding enzymes associated with the synthesis of amino acids with higher enzymatic activity from other species originates.

In some embodiments, the host cell was *Corynebacterium glutamicum*. In some other embodiments, the host cell was *Escherichia* co/i. *Corynebacterium glutamicum* and *Escherichia coli* are both important strains for lysine production. By expressing the aspartate kinase mutant removing the feedback inhibition of lysine in *Corynebacterium glutamicum* and *Escherichia coli*, it is possible to realize highly efficient production of lysine and derivatives thereof.

In some embodiments, the conditions for screening recombinant host cells were as follows: the strains were inoculated with toothpicks into a 96-well plate containing 200 µl fermentation medium in each well and cultured at 30° C. for 24 h. The rotating speed of the plate shaker was 800 rpm.

In some embodiments, the conditions for fermentation culture were as follows: the recombinant host cells were inoculated into a TSB liquid medium and cultured for 6-8 h. The cultures were inoculated as seeds into a 24-well plate containing 600 µl fermentation medium in each well with the initial $OD_{600}$ controlled at about 0.1, and cultured at 30° C. for 17 h. The rotating speed of the plate shaker was 800 rpm. Three samples were set for each strain. After the fermentation, $OD_{600}$ and the lysine yield were measured.

The ingredients of the fermentation medium were as follows: glucose, 80 g/L; yeast powder, 1 g/L; soy peptone, 1 g/L; NaCl, 1 g/L; ammonium sulfate, 1 g/L; urea, 8 g/L; $K_2HPO_4 \cdot 3H_2O$, 1 g/L; $MgSO_4 \cdot 7H_2O$, 0.45 g/L; $FeSO_4 \cdot 7H_2O$, 0.05 g/L; biotin, 0.4 mg/L; vitamin B1, 0.1 mg/L; MOPS, 40 g/L; and initial pH7.2.

In some embodiments, for recovering amino acids from the recombinant host cells or the culture broth of the recombinant cells, a common method in this field may be used, including but not limited to: filtration, anion exchange chromatography, crystallization, and HPLC.

The enzymes catalyzing some or all of the reactions described in the present disclosure may be expressed in non-natural, engineered heterologous organisms. Specifically, genes encoding the enzyme for the synthesis pathway may be isolated, inserted into expression vectors of organisms used for transformation production, and incorporated into a genome, and directly express the enzyme. In this field, the method for manipulating microorganisms are known, such as explained in *Current Protocols in Molecular Biology* (Online ISBN: 9780471142720, John Wiley and Sons, Inc.), *Microbial Metabolic Engineering: Methods and Protocols* (Qiong Cheng Ed., Springer), and *Systems Metabolic Engineering: Methods and Protocols* (Hal S. Alper Ed., Springer). CL EXAMPLES Additional objectives, features, and advantages of the present disclosure are apparent from the subsequent description in detail. However, it is to be appreciated that the detailed description and specific examples (although indicating specific embodiments of the present disclosure) are provided merely for illustrative purpose. Based on the detailed description, various changes and modifications within the spirits and the scopes of the present disclosure will become apparent to a person skilled in the art.

The experimental techniques and experimental methods used in the examples, unless otherwise specified, are all conventional techniques and methods, for example, experimental methods for which no specific conditions are indicated in the following examples are generally performed according to conventional conditions such as those described by Sambrook et al., *Molecular Cloning: A Laboratory Manual* (New York: Cold Spring Harbor Laboratory Press, 1989), or those recommended by manufacturers. The materials, reagents, etc. used in the examples, unless otherwise specified, are all commercially available.

Example 1. Construction of a Library of *Corynebacterium glutamicum* lysC Gene Mutants Based on the sequence and the structural characteristics of *Corynebacterium glutamicum* LysC and the inventor's understanding of its functions, it was presumed that mutations of amino acids at positions 293, 294, 307 could remove lysine feedback inhibition of LysC, and increase L-lysine yield of *Corynebacterium glutamicum.*

For rapid site-directed mutation of *Corynebacterium glutamicum*, the present disclosure firstly constructed an editing system for single-strand recombination-based CRISPR/Cas9 genome. With the pCas9 plasmid [3] as a template and cas9-1/cas9-2 as primers, the operating element lacO mutation (TGTGTGGAATTGTGAGCGGATAACAATTTCACACA mutated to TGTGTGGAATTGTGAGCGCTCACAATTTCACACA) and RBS mutation (AAAGGAGTTGAGA mutated to AAAGGCACCCGAT) were introduced into the primers to amplify the fragments comprising cas9; then, with pnCas9(D10A)-AID-gRNA-ccdB$^{TS}$[4] plasmid as a template and gRNA-1/gRNA-2 as primers, a fragment of the plasmid skeleton comprising a gRNA-ccdB expression cassette and a temperature sensitive replication origin was amplified. The above 2 fragments were ligated via Vazyme's One Step Cloning Kit to obtain a highly efficiently constructed pCas9gRNA-ccdB plasmid. The plasmid had a plasmid vector map as shown in FIG. 1 and a sequence as shown in SEQ ID NO: 3. With the *Corynebacterium glutamicum* ATCC13032 genome as a template and $P_{ddh}$-1/$P_{ddh}$-2 as primers, the ddh gene promoter mutant (ATGCATCTC mutated to ACAAAAGGT) was amplified, of which the sequence is as shown in SEQ ID NO: 4; with the *Escherichia coli* MG1655 genome as a template, the recT gene was amplified; with the pEC-XK99E plasmid as a template and rrnB-1/rrnB-2 as primers, the rrnB terminator fragment was amplified; with the pEC-XK99E plasmid as a template and PEC-1/PEC-2 as primers, a fragment of the plasmid skeleton from which the per gene was knocked out was amplified. The above 4 fragments were ligated via Vazyme's One Step Cloning Kit to obtain a pRecT plasmid that expressing RecT. The plasmid had a plasmid vector map as shown in FIG. 2 and a sequence as shown in SEQ ID NO: 5.

Two pCas9gRNA plasmids respectively targeting positions 293/294 and 307 of the lysC gene were constructed by the Goldengate Cloning method[4] reported in the literature. The target DNA-binding region of gRNA1 was TGCAGAAATCAACATTGACA; the target DNA-binding region of gRNA2 was GCAGGTGAAGGTGATGTCGG The lysC-F1/lysC-R1, lysC-F2/lysC-R2 primers were denatured and annealed, respectively, and then were subjected to Goldengate Cloning together with the pCas9gRNA-ccdB plasmid, obtaining pCas9gRNA-lysC1 and pCas9gRNA-lysC2 plasmid, respectively.

On the basis of the single-stranded recombinant CRISPR/Cas9 genome editing system, a library of lysC gene mutants at amino acid positions 293, 294 and 307 were constructed. The pRecT plasmid was electrotransformed into *Corynebacterium glutamicum* ATCC13032, obtaining the ATCC13032 (pRecT) strain. Competent cells[5] were prepared from ATCC13032 (pRecT) strain using the method reported in the literature. In order to perform 19 mutations other than the wild-type mutations at amino acid positions 293, 294 and 307 of the lysC gene, the single-stranded DNAs of 293-1 to 293-9, 294-1 to 294-9 and that of 307-1 to 307-9 were designed as the recombination template for mutant construction. The competent cells of ATCC13032 (pRecT) were electrotransformed respectively with 1-2 µg pCas9gRNA-lysC1 plasmid and 10 µg single-stranded DNAs of equimolar concentration of the theoretical 19 mutants of 293-1 to 293-9, and with 1-2 µg pCas9gRNA-lysC1 plasmid and 10 µg single-stranded DNAs of equimolar concentration of the theoretical 19 mutants of 294-1 to 294-9, and with 1-2 µg pCas9gRNA-lysC2 plasmid and 10 µg single-stranded DNAs of equimolar concentration of the theoretical 19 mutants of 307-1 to 307-9, and then added into 1 mL TSB culture medium pre-heated at 46° C., subjected to heat shock at 46° C. for 6 min, incubated at 30° C. for 3 h, coated on TSB plates supplemented with 5 µg/mL chloramphenicol and 0.05 mM IPTG and incubated for 2 days, to grow hundreds of clones, obtaining a library of mutants at amino acid positions 293, 294 and 307, respectively. The ingredients (g/L) of the TSB liquid medium were as follows: glucose, 5 g/L; yeast powder, 5 g/L; soy peptone, 9 g/L; urea, 3 g/L; succinic acid, 0.5 g/L; $K_2HPO_4 \cdot 3H_2O$, 1 g/L; $MgSO_4 \cdot 7H_2O$, 0.1 g/L; biotin, 0.01 mg/L; vitamin B1, 0.1 mg/L; MOPS, 20 g/L. The solid medium was supplemented with 15 g/L FO agar powder. The sequences of the primers used above are as shown in Table 2.

TABLE 2

| Primer | Nucleotide Sequence | SEQ ID NO. |
|---|---|---|
| cas9-1 | GCGCTCACAATTTCACACAGGAAACAGAATTAATTAAGCT TAAAGGCACCCGATATGGATAAGAAATACTCAATAGGC | SEQ ID NO: 6 |
| cas9-2 | TCAGTCACCTCCTAGCTGACTCAAATC | SEQ ID NO: 7 |
| gRNA-1 | GTCAGCTAGGAGGTGACTGAAGCTTGGCTGTTTTGGCGGA TG | SEQ ID NO: 8 |
| gRNA-2 | CTGTGTGAAATTGTGAGCGCTCACAATTCC | SEQ ID NO: 9 |

TABLE 2-continued

| Primer | Nucleotide Sequence | SEQ ID NO. |
|---|---|---|
| $P_{ddh}$-1 | CTGTGCGGTATTTCACACCGGTGCGTGGCGAGTTTTACAA AG | SEQ ID NO: 10 |
| $P_{ddh}$-2 | GTTCTTGTAATCCTCCAAAATTGTGGTGGCACTGTCCTGGT CGAGCTTACCACCTTTTGTACTTAGATGATGATTCAGGGAC | SEQ ID NO: 11 |
| recT-1 | TTTTGGAGGATTACAAGAACATGACTAAGCAACCACCAAT CGC | SEQ ID NO: 12 |
| recT-2 | TTCCTCTGAATTATCGATTACACTG | SEQ ID NO: 13 |
| rrnB-1 | TAATCGATAATTCAGAGGAATAACTGTTTTGGCGGATGAGA GAAG | SEQ ID NO: 14 |
| rrnB-2 | GGAGACCTTTTTGGAGCTAGTCG | SEQ ID NO: 15 |
| PEC-1 | CTAGCTCCAAAAAGGTCTCCAGG | SEQ ID NO: 16 |
| PEC-2 | CGGTGTGAAATACCGCACAGATG | SEQ ID NO: 17 |
| lysC-F1 | TTCATGCAGAAATCAACATTGACA | SEQ ID NO: 18 |
| lysC-R1 | AAACTGTCAATGTTGATTTCTGCA | SEQ ID NO: 19 |
| lysC-F2 | TTCAGCAGGTGAAGGTGATGTCGG | SEQ ID NO: 20 |
| lysC-R2 | AAACCCGACATCACCTTCACCTGC | SEQ ID NO: 21 |
| 293-1 | GGTGGTGCCGTCTTCTACAGAAGAGACGTTCTGCAGAACC ATGTCGARGTTGATTTCTGCATCAGCCAACGCACGGAAAA CCTTCGCAGC | SEQ ID NO: 22 |
| 293-2 | GGTGGTGCCGTCTTCTACAGAAGAGACGTTCTGCAGAACC ATGTCCWTGTTGATTTCTGCATCAGCCAACGCACGGAAAA CCTTCGCAGC | SEQ ID NO: 23 |
| 293-3 | GGTGGTGCCGTCTTCTACAGAAGAGACGTTCTGCAGAACC ATGTCGGHGTTGATTTCTGCATCAGCCAACGCACGGAAAA CCTTCGCAGC | SEQ ID NO: 24 |
| 293-4 | GGTGGTGCCGTCTTCTACAGAAGAGACGTTCTGCAGAACC ATGTCGTDGTTGATTTCTGCATCAGCCAACGCACGGAAAA CCTTCGCAGC | SEQ ID NO: 25 |
| 293-5 | GGTGGTGCCGTCTTCTACAGAAGAGACGTTCTGCAGAACC ATGTCTKGGTTGATTTCTGCATCAGCCAACGCACGGAAAA CCTTCGCAGC | SEQ ID NO: 26 |
| 293-6 | GGTGGTGCCGTCTTCTACAGAAGAGACGTTCTGCAGAACC ATGTCWTCGTTGATTTCTGCATCAGCCAACGCACGGAAAA CCTTCGCAGC | SEQ ID NO: 27 |
| 293-7 | GGTGGTGCCGTCTTCTACAGAAGAGACGTTCTGCAGAACC ATGTCGCVGTTGATTTCTGCATCAGCCAACGCACGGAAAA CCTTCGCAGC | SEQ ID NO: 28 |
| 293-8 | GGTGGTGCCGTCTTCTACAGAAGAGACGTTCTGCAGAACC ATGTCGACGTTGATTTCTGCATCAGCCAACGCACGGAAAA CCTTCGCAGC | SEQ ID NO: 29 |
| 293-9 | GGTGGTGCCGTCTTCTACAGAAGAGACGTTCTGCAGAACC ATGTCCCAGTTGATTTCTGCATCAGCCAACGCACGGAAAA CCTTCGCAGC | SEQ ID NO: 30 |
| 294-1 | GTCGGTGGTGCCGTCTTCTACAGAAGAGACGTTCTGCAGA ACCATGADAATGTTGATTTCTGCATCAGCCAACGCACGGA AAACCTTCGC | SEQ ID NO: 31 |

TABLE 2-continued

| Primer | Nucleotide Sequence | SEQ ID NO. |
|---|---|---|
| 294-2 | GTCGGTGGTGCCGTCTTCTACAGAAGAGACGTTCTGCAGAACCATCWTAATGTTGATTTCTGCATCAGCCAACGCACGGAAAACCTTCGC | SEQ ID NO: 32 |
| 294-3 | GTCGGTGGTGCCGTCTTCTACAGAAGAGACGTTCTGCAGAACCATGGHAATGTTGATTTCTGCATCAGCCAACGCACGGAAAACCTTCGC | SEQ ID NO: 33 |
| 294-4 | GTCGGTGGTGCCGTCTTCTACAGAAGAGACGTTCTGCAGAACCATGTDAATGTTGATTTCTGCATCAGCCAACGCACGGAAAACCTTCGC | SEQ ID NO: 34 |
| 294-5 | GTCGGTGGTGCCGTCTTCTACAGAAGAGACGTTCTGCAGAACCATTKGAATGTTGATTTCTGCATCAGCCAACGCACGGAAAACCTTCGC | SEQ ID NO: 35 |
| 294-6 | GTCGGTGGTGCCGTCTTCTACAGAAGAGACGTTCTGCAGAACCATTTCAATGTTGATTTCTGCATCAGCCAACGCACGGAAAACCTTCGC | SEQ ID NO: 36 |
| 294-7 | GTCGGTGGTGCCGTCTTCTACAGAAGAGACGTTCTGCAGAACCATGCVAATGTTGATTTCTGCATCAGCCAACGCACGGAAAACCTTCGC | SEQ ID NO: 37 |
| 294-8 | GTCGGTGGTGCCGTCTTCTACAGAAGAGACGTTCTGCAGAACCATGACAATGTTGATTTCTGCATCAGCCAACGCACGGAAAACCTTCGC | SEQ ID NO: 38 |
| 294-9 | GTCGGTGGTGCCGTCTTCTACAGAAGAGACGTTCTGCAGAACCATCCAAATGTTGATTTCTGCATCAGCCAACGCACGGAAAACCTTCGC | SEQ ID NO: 39 |
| 307-1 | CGCGCGGCGGCCGTCGGAACGAGGGCAGGTGAAGGTGATGTCGGTGADGCCGTCTTCTACAGAAGAGACGTTCTGCAGAACCATGTCAAT | SEQ ID NO: 40 |
| 307-2 | CGCGCGGCGGCCGTCGGAACGAGGGCAGGTGAAGGTGATGTCGGTCWTGCCGTCTTCTACAGAAGAGACGTTCTGCAGAACCATGTCAAT | SEQ ID NO: 41 |
| 307-3 | CGCGCGGCGGCCGTCGGAACGAGGGCAGGTGAAGGTGATGTCGGTAGMGCCGTCTTCTACAGAAGAGACGTTCTGCAGAACCATGTCAAT | SEQ ID NO: 42 |
| 307-4 | CGCGCGGCGGCCGTCGGAACGAGGGCAGGTGAAGGTGATGTCGGTGTDGCCGTCTTCTACAGAAGAGACGTTCTGCAGAACCATGTCAAT | SEQ ID NO: 43 |
| 307-5 | CGCGCGGCGGCCGTCGGAACGAGGGCAGGTGAAGGTGATGTCGGTTKGGCCGTCTTCTACAGAAGAGACGTTCTGCAGAACCATGTCAAT | SEQ ID NO: 44 |
| 307-6 | CGCGCGGCGGCCGTCGGAACGAGGGCAGGTGAAGGTGATGTCGGTWTCGCCGTCTTCTACAGAAGAGACGTTCTGCAGAACCATGTCAAT | SEQ ID NO: 45 |
| 307-7 | CGCGCGGCGGCCGTCGGAACGAGGGCAGGTGAAGGTGATGTCGGTGCVGCCGTCTTCTACAGAAGAGACGTTCTGCAGAACCATGTCAAT | SEQ ID NO: 46 |
| 307-8 | CGCGCGGCGGCCGTCGGAACGAGGGCAGGTGAAGGTGATGTCGGTGACGCCGTCTTCTACAGAAGAGACGTTCTGCAGAACCATGTCAAT | SEQ ID NO: 47 |
| 307-9 | CGCGCGGCGGCCGTCGGAACGAGGGCAGGTGAAGGTGATGTCGGTCCAGCCGTCTTCTACAGAAGAGACGTTCTGCAGAACCATGTCAAT | SEQ ID NO: 48 |
| lysC-C1 | CGGACGTTGACGGTGTGTATAC | SEQ ID NO: 49 |
| lysC-C2 | GCACGGAAATACGAATCTCAGAG | SEQ ID NO: 50 |

Example 2. Screening and Sequencing of the Library of *Corynebacterium glutamicum* lysC Gene Mutants In order to screen the library of *Corynebacterium glutamicum* lysC gene mutants, 60 clones were selected for each of positions 293, 294 and 307 from the library of mutants and subjected to fermentation, so as to screen the mutants of high L-lysine yield. The ingredients of the fermentation medium were as follows: glucose, 80 g/L; yeast powder, 1 g/L; soy peptone, 1 g/L; NaCl, 1 g/L; ammonium sulfate, 1 g/L; urea, 8 g/L; $K_2HPO_4 \cdot 3H_20$, 1 g/L; $MgSO_4 \cdot 7H_2O$, 0.45 g/L; $FeSO_4 \cdot$-$7H_20$, 0.05 g/L; biotin, 0.4 mg/L; vitamin B1, 0.1 mg/L; MOPS, 40 g/L; and initial pH7.2. The strains were inoculated with toothpicks into a 96-well plate containing 200 µl fermentation medium in each well and cultured at 30° C. for 24 h. The rotating speed of the plate shaker was 800 rpm. After completion of fermentation, L-lysine yield was measured. All clones from the library of position 293 mutants had a yield higher than 0.5 g/L; some clones from the library of position 294 mutants and position 307 mutants had a yield higher than 0.5 g/L, indicating that mutants with mutations of the above positions can remove lysine feedback inhibition and increase lysine production. The mutants obtaining a lysine yield higher than 0.5 g/L, and some mutants from the library of position 294 mutants and position 307 mutants which did not produce lysine were subjected to sequencing analysis by PCR amplification of a target band using lysC-C1/lysC-C2 (Table 2) primers. The yield of the mutants and the sequencing results were as shown in Table 3. Some clones had identical mutations. Finally, 11 mutants were obtained from position 293 mutants, 6 obtained from position 294 mutants, and 5 obtained from position 307 mutants.

TABLE 3

| Strain number | L-lysine yield | Corresponding codon mutation | Amino acid mutation |
|---|---|---|---|
| 293-M1 | ++++ | TCC | I293S |
| 293-M2 | ++++ | GGC | I293G |
| 293-M3 | ++++ | GAA | I293E |
| 293-M4 | ++++ | CCA | I293P |
| 293-M5 | ++++ | TGG | I293W |
| 293-M6 | ++++ | TAC | I293Y |
| 293-M7 | ++++ | CAC | I293H |
| 293-M8 | ++++ | ATG | I293M |
| 293-M9 | ++++ | CAA | I293Q |
| 293-M10 | + | TGC | I293C |
| 293-M11 | ++ | CGC | I293R |
| 294-M1 | + | TAC | D294Y |
| 294-M2 | ++ | TGG | D294W |
| 294-M3 | +++ | TTC | D294F |
| 294-M4 | – | CTC | D294L |
| 294-M5 | – | GTC | D294V |
| 294-M6 | – | TGC | D294C |
| 307-M1 | + | TAC | T307Y |
| 307-M2 | +++ | GGC | T307G |
| 307-M3 | + | TTC | T307F |
| 307-M4 | – | GAA | T307E |
| 307-M5 | – | AAG | T307K |

Note:
–: no lysine produced;
+: lysine yield ranging 0.5 to 1.0 g/L;
++: lysine yield ranging 1.0 to 2.0 g/L;
+++: lysine yield ranging 2.0 to 3.0 g/L;
++++: lysine yield ranging 3.0 to 4.0 g/L.

Example 3. Assessment of Lysine Production of *Corynebacterium glutamicum* lysC Gene Mutants Since the strains previously used for screening mutants based on lysine yield included pRecT and pCas9gRNA-lysC1 or pCas9gRNA-lysC2 plasmid, thus in this example, the above plasmids were deleted, and strains that only having mutations in the genome were obtained and the lysine yield of these strains were assessed. The relatively high-yield strain 293-M1 to strain 293-M9, strain 293-M1 to strain 293-M3, strain 307-M1 to strain 307-M2 were cultured in a chloromycetin-free TSB medium, with two plasmids deleted, respectively obtaining mutant strains of ZCgLJ1 to ZCgLJ9, ZCgLJ11 to ZCgLJ13, ZCgLJ14 to ZCgLJ15 with the plasmids deleted. For the purpose of effect comparison, a huge amount of lysC$^{T311I}$ mutants reported in prior literature that effectively remove lysine feedback inhibition were constructed at the same time. Such strains were obtained by introducing T311I (i.e. the bases mutated from ACC to ATC) amino acid mutation into the lysC gene encoding aspartate kinase of *Corynebacterium glutamicum* ATCC13032 (Reference Document 2). Further, the wild-type *Corynebacterium glutamicum* ATCC13032 was used as the control strain (WT). A 24-well plate was used to assess the lysine production of the strains. The strains were firstly inoculated into the TSB liquid medium and cultured for 6-8. The cultures were inoculated as seeds into a 24-well plate containing 600 µl of fermentation medium in each well (the same as in Example 2) with the initial $OD_{600}$ controlled at about 0.1, and cultured at 30° C. for 17 h. The rotating speed of the plate shaker was 800 rpm. Three samples were set for each strain. After the fermentation, the lysine yield was measured. The results were listed in Table 4. All of the 11 mutants with mutation at position 293 had higher yield than the T311I control mutant. D294F (ZCgLJ13 strain) mutants with mutation at position 294 and T307G (ZCgLJ15) mutants with mutation at position 307 also had higher yield than the T311I control mutant. Mutations at these amino acid positions were more promising in application of the production of amino acids and derivatives thereof than T311I, in particular in the production of lysine, threonine and isoleucine and derivatives thereof such as pentanediamine, 5-aminovaleric acid, glutaric acid, hydroxyisoleucine, which all rely on LysC catalyzing reactions.

TABLE 4

| Strain | Amino acid mutation | $OD_{600}$ | lysine yield (g/L) |
|---|---|---|---|
| WT | — | 11.78 ± 0.18 | 0.17 ± 0.06 |
| lysC$^{T311I}$ | T311I | 12.15 ± 0.23 | 2.33 ± 0.06 |
| ZCgLJ1 | I293S | 12.50 ± 0.35 | 3.27 ± 0.15 |
| ZCgLJ2 | I293G | 11.99 ± 0.34 | 3.00 ± 0.10 |
| ZCgLJ3 | I293E | 11.86 ± 0.59 | 3.00 ± 0.20 |
| ZCgLJ4 | I293P | 12.22 ± 0.55 | 3.30 ± 0.20 |
| ZCgLJ5 | I293W | 12.35 ± 0.03 | 3.33 ± 0.06 |
| ZCgLJ6 | I293Y | 12.72 ± 0.24 | 3.53 ± 0.06 |
| ZCgLJ7 | I293H | 12.40 ± 0.08 | 3.30 ± 0.00 |
| ZCgLJ8 | I293M | 12.15 ± 0.25 | 2.77 ± 0.06 |
| ZCgLJ9 | I293Q | 12.23 ± 0.06 | 3.50 ± 0.00 |
| ZCgLJ11 | D294Y | 12.00 ± 0.51 | 0.60 ± 0.00 |
| ZCgLJ12 | D294W | 12.04 ± 0.41 | 1.73 ± 0.06 |
| ZCgLJ13 | D294F | 12.66 ± 0.20 | 2.73 ± 0.06 |
| ZCgLJ14 | T307Y | 12.14 ± 0.41 | 0.7 ± 0.00 |
| ZCgLJ15 | T307G | 12.41 ± 0.18 | 2.50 ± 0.00 |

All technical features disclosed herein are able to be combined to form any combination. Each feature disclosed herein may be substituted by a feature having an identical, equivalent, or similar function. Therefore, unless otherwise specified, each feature disclosed herein is merely a practical example of a series of equivalent or similar features.

In addition, based on the foregoing description of the present disclosure, a person skilled in the art clearly knows the key features of the present disclosure. Without departing from the spirits and scopes of the present disclosure, a number of alterations may be made to the invention to adapt to different purposes and conditions of use. Therefore, it is intended that such alterations also fall in the scope of attached claims.

REFERENCE

[1] Bearer CF, Neet KE; Stadtman, E. R., Cohen, G N., LeBras, G, Robichon-Szulmajster, H. (1961). "Feed-back Inhibition and Repression of Aspartokinase Activity in *Escherichia coli* and *Saccharomyces cerevisiae*". J. Biol. Chem.

[2] Watson et. al. (1987) *Molecular Biology of the Gene*. Fourth Edition. Benjamin/Cummings Pub. Co. P224.

[3] LIU, Jiao, et al. "Development of a CRISPR/Cas9 genome editing toolbox for *Corynebacterium glutamicum*". Microbial cell factories, 2017, 16.1: 205.

[4] WANQ Yu, et al. "Expanding targeting scope, editing window, and base transition capability of base editing in *Corynebacterium glutamicum*". Biotechnology and bioengineering, 2019, 116: 3016-3029.

[5] Ruan Y, Zhu L, Li Q. "Improving the electro-transformation efficiency of *Corynebacterium glutamicum* by weakening its cell wall and increasing the cytoplasmic membrane fluidity". Biotechnol Lett. 2015; 37: 2445-52.

What is claimed is:

1. A polypeptide having an aspartate kinase activity, wherein the polypeptide comprises an amino acid sequence as shown in SEQ ID NO: 1, wherein the polypeptide further comprises a mutation in the amino acid sequence, as shown in at least one group of (a) to (c) as follows:

(a) the amino acid residue at a position in the amino acid sequence corresponding to position 293 of SEQ ID NO: 1 is mutated from isoleucine (I) to serine (S), glycine (G), glutamic acid (E), proline (P), tryptophan (W), tyrosine (Y), histidine (H), methionine (M), glutamine (Q), cysteine (C), or arginine (R);

(b) the amino acid residue at a position in the amino acid sequence corresponding to position 294 of SEQ ID NO: 1 is mutated from aspartic acid (D) to tyrosine (Y), tryptophan (W), or phenylalanine (F); and (c) the amino acid residue at a position in the amino acid sequence corresponding to position 307 of SEQ ID NO: 1 is mutated from threonine (T) to tyrosine (Y), glycine (G), or phenylalanine (F).

2. The polypeptide according to claim 1, wherein the polypeptide comprises a deletion or an addition of at least one amino acid residue at the N-terminus or C-terminus of the polypeptide.

3. A recombinant polypeptide comprising the polypeptide according to claim 1 and an exogenous polypeptide fused to the polypeptide.

4. A method for producing an amino acid, comprising:

(a) producing the amino acid using the polypeptide according to claim 1; and (b) purifying or isolating the amino acid;

wherein the amino acid is selected from lysine, threonine, isoleucine and an amino acid derivative thereof, wherein the amino acid derivative thereof comprises at least one of pentanediamine, 5-aminovaleric acid, glutaric acid, and hydroxyisoleucine.

5. The recombinant polypeptide according to claim 3, wherein the exogenous polypeptide comprises a tag polypeptide and a spacer polypeptide linking the tag polypeptide to the polypeptide having the aspartate kinase activity.

6. The recombinant polypeptide according to claim 3, wherein the exogenous polypeptide comprises a tag polypeptide.

7. The polypeptide according to claim 1, wherein the amino acid residue at a position in the amino acid sequence corresponding to position 293 of SEQ ID NO: 1 is substituted from isoleucine (I) to serine (S), glycine (G), glutamic acid (E), proline (P), tryptophan (W), tyrosine (Y), histidine (H), methionine (M), glutamine (Q), cysteine (C), or arginine (R).

8. The polypeptide according to claim 1, wherein the amino acid residue at a position in the amino acid sequence corresponding to position 294 of SEQ ID NO: 1 is substituted from aspartic acid (D) to tyrosine (Y), tryptophan (W), or phenylalanine (F).

9. The polypeptide according to claim 1, wherein the amino acid residue at a position in the amino acid sequence corresponding to position 307 of SEQ ID NO: 1 is substituted from threonine (T) to tyrosine (Y), glycine (G), or phenylalanine (F).

10. The polypeptide according to claim 1, wherein the polypeptide comprises two mutations in the amino acid sequence, as shown in any two groups of (a) to (c) as follows:

(a) the amino acid residue at a position in the amino acid sequence corresponding to position 293 of SEQ ID NO: 1 is mutated from isoleucine (I) to serine (S), glycine (G), glutamic acid (E), proline (P), tryptophan (W), tyrosine (Y), histidine (H), methionine (M), glutamine (Q), cysteine (C), or arginine (R);

(b) the amino acid residue at a position in the amino acid sequence corresponding to position 294 of SEQ ID NO: 1 is mutated from aspartic acid (D) to tyrosine (Y), tryptophan (W), or phenylalanine (F); and (c) the amino acid residue at a position in the amino acid sequence corresponding to position 307 of SEQ ID NO: 1 is mutated from threonine (T) to tyrosine (Y), glycine (G), or phenylalanine (F).

11. The polypeptide according to claim 1, wherein the polypeptide comprises three mutations in the amino acid sequence, as shown in groups (a) to (c) as follows:

(a) the amino acid residue at a position in the amino acid sequence corresponding to position 293 of SEQ ID NO: 1 is mutated from isoleucine (I) to serine (S), glycine (G), glutamic acid (E), proline (P), tryptophan (W), tyrosine (Y), histidine (H), methionine (M), glutamine (Q), cysteine (C), or arginine (R);

(b) the amino acid residue at a position in the amino acid sequence corresponding to position 294 of SEQ ID NO: 1 is mutated from aspartic acid (D) to tyrosine (Y), tryptophan (W), or phenylalanine (F); and (c) the amino acid residue at a position in the amino acid sequence corresponding to position 307 of SEQ ID NO: 1 is mutated from threonine (T) to tyrosine (Y), glycine (G), or phenylalanine (F).

* * * * *